United States Patent [19]
Gordon et al.

[11] Patent Number: 6,048,351
[45] Date of Patent: Apr. 11, 2000

[54] TRANSVAGINAL SUTURING SYSTEM

[75] Inventors: Norman S. Gordon, Irvine; Robert P. Cooper, Yorba Linda; Richard L. Quick, Trabuco Canyon, all of Calif.

[73] Assignee: Scimed Life Systems, Inc., Maple Grove, Minn.

[21] Appl. No.: 09/058,530

[22] Filed: Apr. 10, 1998

Related U.S. Application Data

[63] Continuation-in-part of application No. 09/002,875, Jan. 5, 1998, abandoned, which is a continuation of application No. 08/554,743, Nov. 7, 1995, Pat. No. 5,713,910, which is a continuation-in-part of application No. 08/311,967, Sep. 26, 1994, Pat. No. 5,578,044, which is a continuation-in-part of application No. 08/205,042, Mar. 2, 1994, Pat. No. 5,540,704, which is a continuation-in-part of application No. 08/057,699, May 4, 1993, Pat. No. 5,458,609, which is a continuation-in-part of application No. 07/941,382, Sep. 4, 1992, Pat. No. 5,364,408.

[51] Int. Cl.⁷ .................................................. A61B 17/04
[52] U.S. Cl. .......................... 606/144; 606/139; 606/147; 112/169
[58] Field of Search ..................... 606/139, 144, 606/145, 147; 112/169

[56] References Cited

U.S. PATENT DOCUMENTS

| 342,773 | 6/1886 | Bailey . |
|---|---|---|
| 919,138 | 4/1909 | Drake et al. . |

(List continued on next page.)

FOREIGN PATENT DOCUMENTS

| 647813 | 9/1962 | Canada . |
|---|---|---|
| 0 140 557 | 5/1985 | European Pat. Off. . |
| 0 589 409 | 3/1994 | European Pat. Off. . |
| 0 674 875 | 10/1995 | European Pat. Off. . |
| 969254 | 10/1982 | U.S.S.R. . |
| 1028320 | 7/1983 | U.S.S.R. . |
| 1093329 | 5/1984 | U.S.S.R. . |
| 18602 | 9/1909 | United Kingdom . |
| 2 247 841 | 3/1992 | United Kingdom . |
| 2 268 690 | 1/1994 | United Kingdom . |
| WO/90/03766 | 4/1990 | WIPO . |
| WO/92/12674 | 8/1992 | WIPO . |
| WO/93/01750 | 2/1993 | WIPO . |
| WO/94/05123 | 3/1994 | WIPO . |
| WO/94/13211 | 6/1994 | WIPO . |

OTHER PUBLICATIONS

Description of "Rema Deep Suture", publication status and dates unknown, original document in German, English translation attached.

*Primary Examiner*—Gary Jackson
*Attorney, Agent, or Firm*—Testa, Hurwitz & Thibeault, LLP

[57] ABSTRACT

A method and device for the placement of sutures and for the purpose of approximating tissue. The invention relates to devices for approximation, ligation and fixation of tissue using a suture, to various constituent parts comprising said devices, and particularly to the placement of sutures into certain difficult to access ligamental structures, to the approximation of tissue separated by means of an endosurgical trocar being inserted into a body cavity, and to approximation, ligation, and fixation of body tissue using both traditional open surgical and endosurgical techniques and instruments. The invention provides for the loading of suture material including needles into the device, introduction and placement of the device into the body cavity, with the distal end having deployable needle guides, extending the needle guides either simultaneously or individually to the periphery of the wound, engaging the wound with the needle guides, driving the needles and suture material through the tissue to be approximated into a catch mechanism, retracting the needle guides and withdrawing the device, leaving a loop of suture material in the margin of tissue. The suture may then be tied to approximate the wound and excess suture material cut off. The invention also provides for the placement of sutures for the endoscopic approximation, fixation, and ligation of tissues within a body cavity including the driving and retrieval of needle and suture combinations, and facilitating the tying of knots.

26 Claims, 14 Drawing Sheets

U.S. PATENT DOCUMENTS

| | | |
|---|---|---|
| 1,037,864 | 9/1912 | Carlson et al. . |
| 1,449,087 | 3/1923 | Bugbee . |
| 1,815,725 | 7/1931 | Pilling et al. . |
| 1,822,330 | 9/1931 | Ainslie . |
| 2,577,240 | 12/1951 | Findley . |
| 2,579,192 | 12/1951 | Kohl . |
| 3,013,559 | 12/1961 | Thomas . |
| 3,160,157 | 12/1964 | Chisman . |
| 3,470,875 | 10/1969 | Johnson . |
| 3,638,653 | 2/1972 | Berry . |
| 3,840,017 | 10/1974 | Violante . |
| 3,918,455 | 11/1975 | Coplan . |
| 3,946,740 | 3/1976 | Bassett . |
| 4,161,951 | 7/1979 | Scanlan, Jr. . |
| 4,164,225 | 8/1979 | Johnson et al. . |
| 4,224,947 | 9/1980 | Fukuda . |
| 4,235,177 | 11/1980 | Arbuckle . |
| 4,236,470 | 12/1980 | Stenson . |
| 4,312,337 | 1/1982 | Donhue . |
| 4,345,601 | 8/1982 | Fududa . |
| 4,493,323 | 1/1985 | Albright et al. . |
| 4,548,202 | 10/1985 | Duncan . |
| 4,557,265 | 12/1985 | Andersson . |
| 4,596,249 | 6/1986 | Freda et al. . |
| 4,602,635 | 7/1986 | Mulhollan et al. . |
| 4,621,640 | 11/1986 | Mulhollan et al. . |
| 4,635,638 | 1/1987 | Weintraub et al. . |
| 4,762,260 | 8/1988 | Richards et al. . |
| 4,781,190 | 11/1988 | Lee . |
| 4,890,615 | 1/1990 | Caspari et al. . |
| 4,898,155 | 2/1990 | Ovil et al. . |
| 4,899,746 | 2/1990 | Brunk . |
| 4,923,461 | 5/1990 | Caspari et al. . |
| 4,926,860 | 5/1990 | Stice et al. . |
| 4,935,027 | 6/1990 | Yoon . |
| 4,957,498 | 9/1990 | Caspari et al. . |
| 5,037,433 | 8/1991 | Wilk et al. . |
| 5,047,039 | 9/1991 | Avant et al. . |
| 5,067,957 | 11/1991 | Jervis . |
| 5,100,415 | 3/1992 | Hayhurst . |
| 5,100,418 | 3/1992 | Yoon et al. . |
| 5,100,421 | 3/1992 | Christoudias . |
| 5,100,498 | 3/1992 | Takeuchi et al. . |
| 5,188,636 | 2/1993 | Fedotov . |
| 5,258,011 | 11/1993 | Drews . |
| 5,306,281 | 4/1994 | Beurrier . |
| 5,308,353 | 5/1994 | Beurrier . |
| 5,324,298 | 6/1994 | Phillips et al. . |
| 5,364,408 | 11/1994 | Gordon . |
| 5,387,221 | 2/1995 | Bisgaard . |
| 5,389,103 | 2/1995 | Melzer et al. . |
| 5,391,174 | 2/1995 | Weston . |
| 5,417,699 | 5/1995 | Klein et al. . |
| 5,458,609 | 10/1995 | Gordon et al. . |
| 5,527,321 | 6/1996 | Hinchliffe . |
| 5,540,704 | 7/1996 | Gordon et al. ............................ 606/144 |
| 5,573,542 | 11/1996 | Stevens . |
| 5,575,800 | 11/1996 | Gordon .................................... 606/144 |
| 5,578,044 | 11/1996 | Gordon et al. ............................ 606/144 |
| 5,662,664 | 9/1997 | Gordon et al. ............................ 606/144 |
| 5,700,272 | 12/1997 | Gordon et al. ............................ 606/144 |
| 5,713,910 | 2/1998 | Gordon et al. ............................ 606/144 |
| 5,741,277 | 4/1998 | Gordon et al. ............................ 606/144 |
| 5,741,279 | 4/1998 | Gordon et al. ............................ 606/144 |

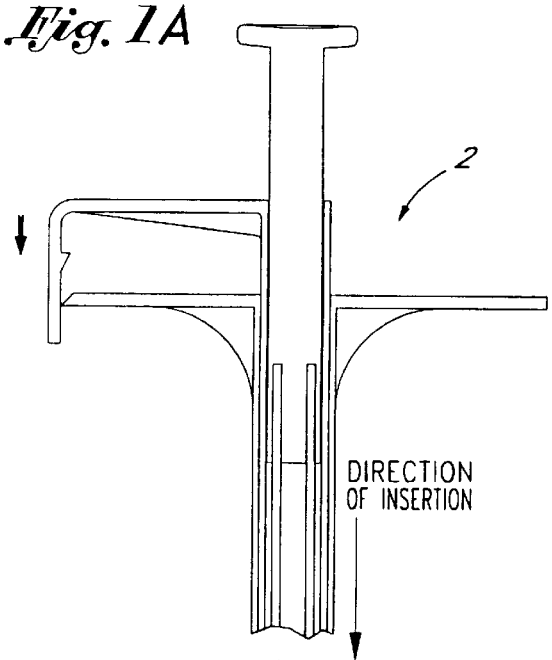
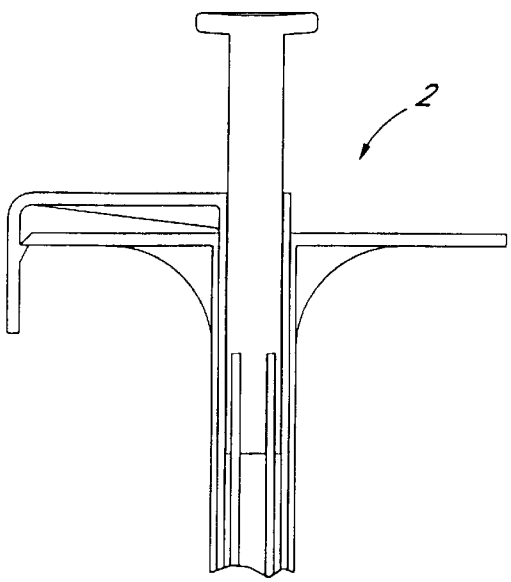
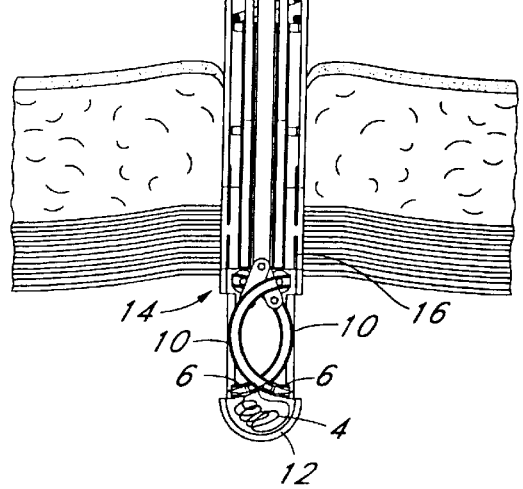
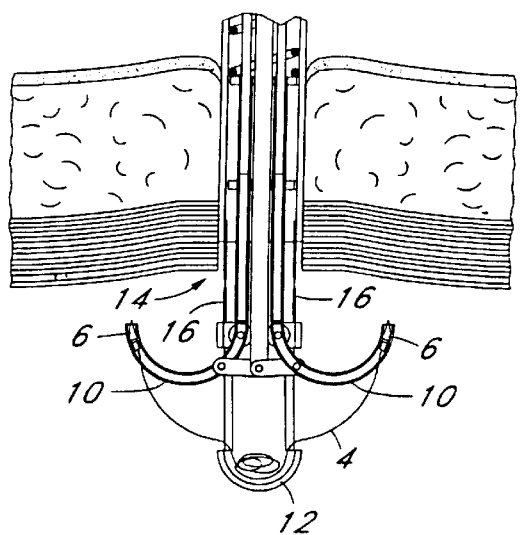

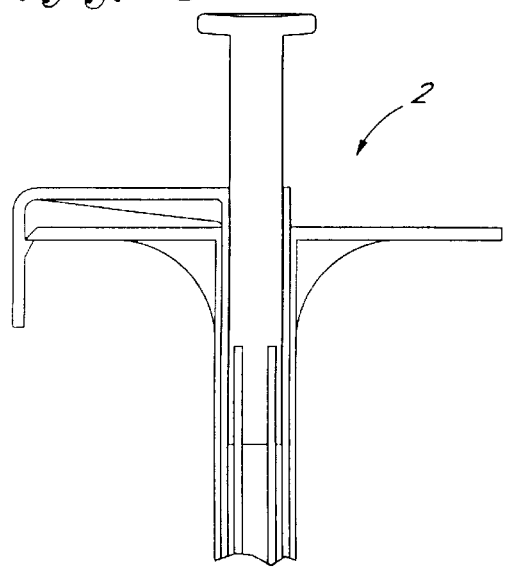
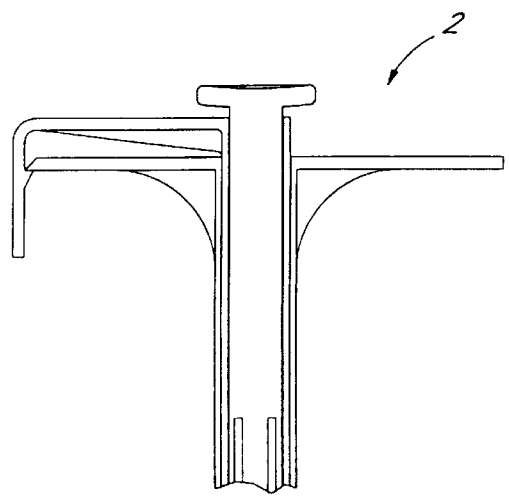

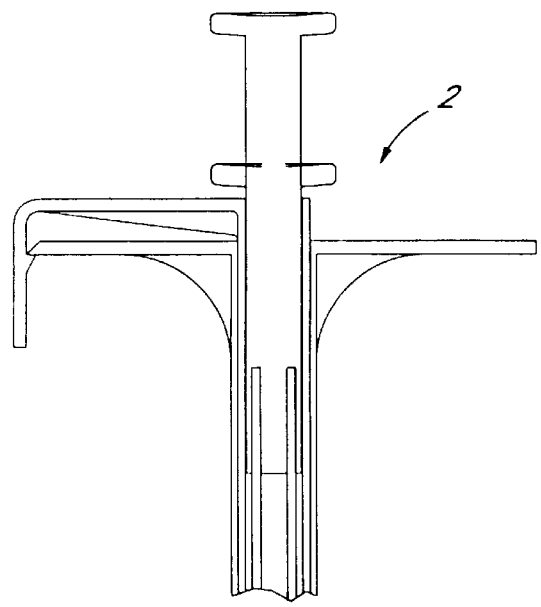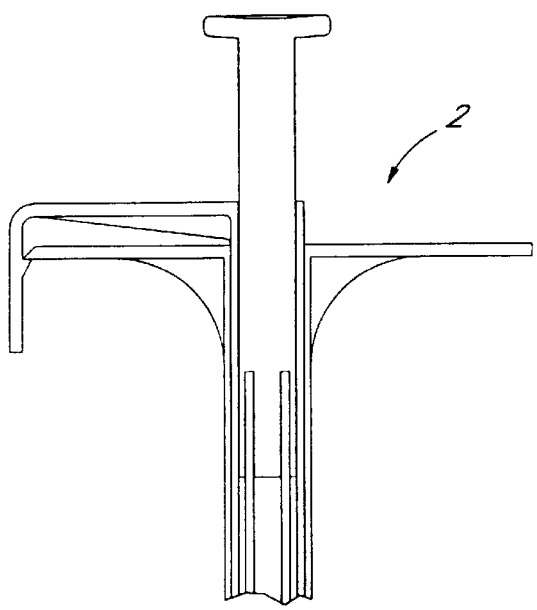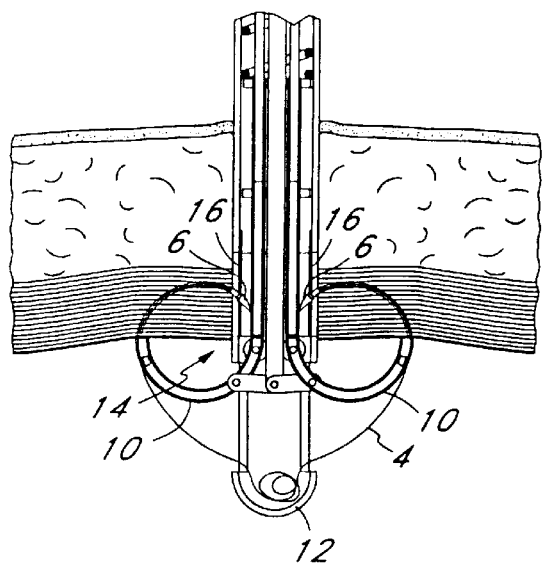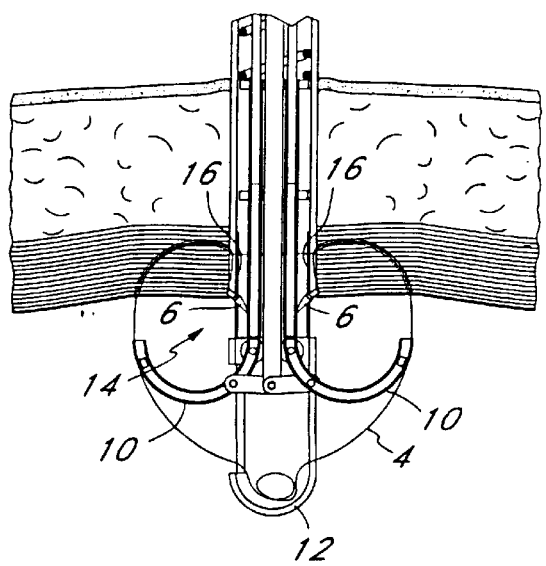

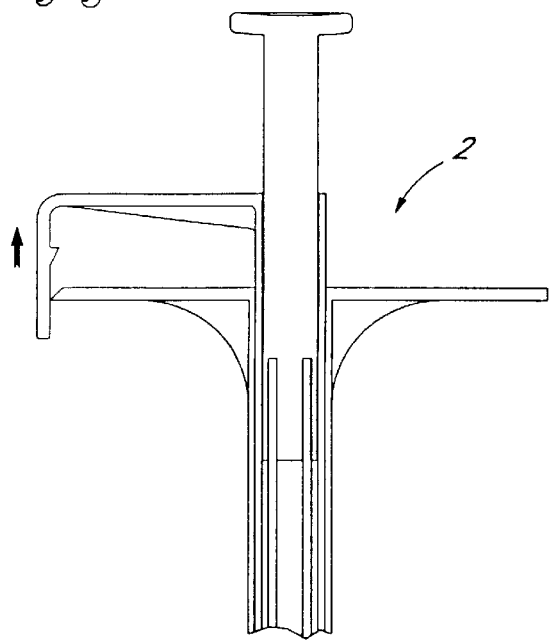
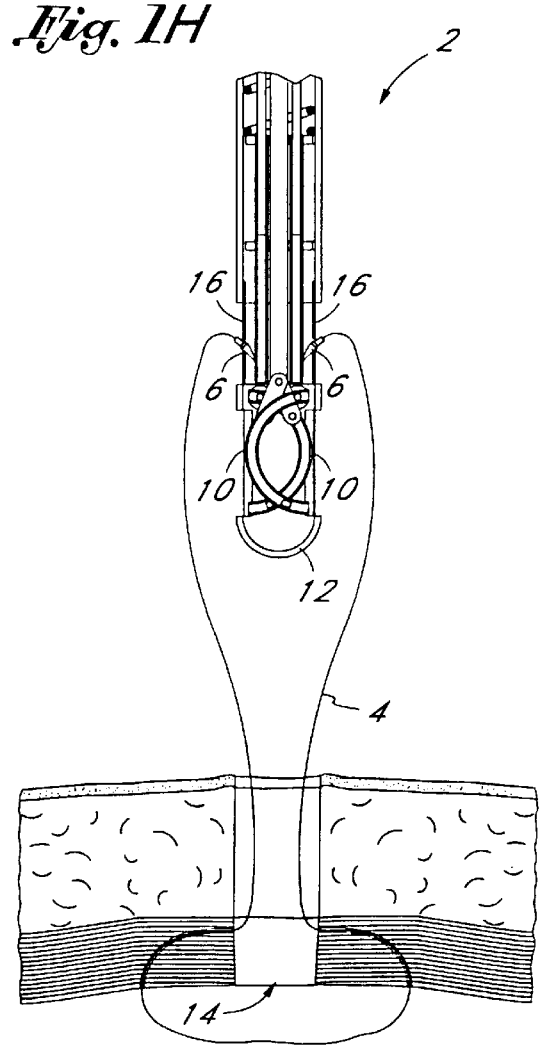
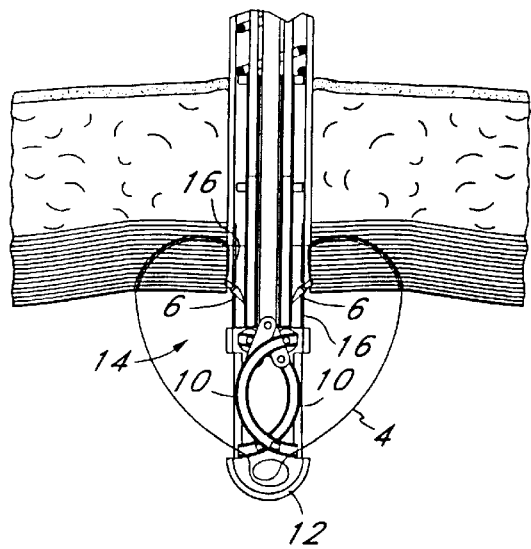
Fig. 1G
Fig. 1H

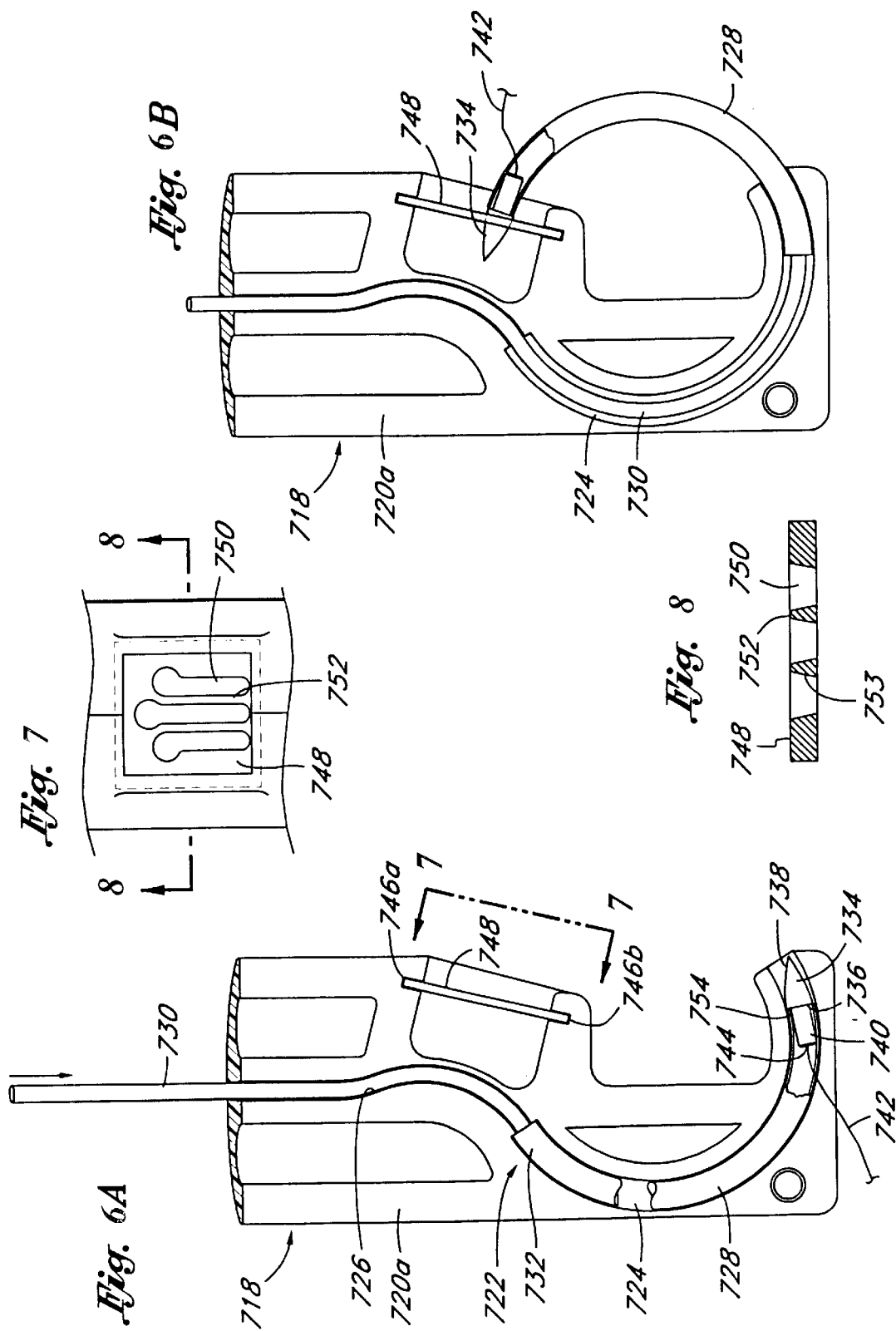

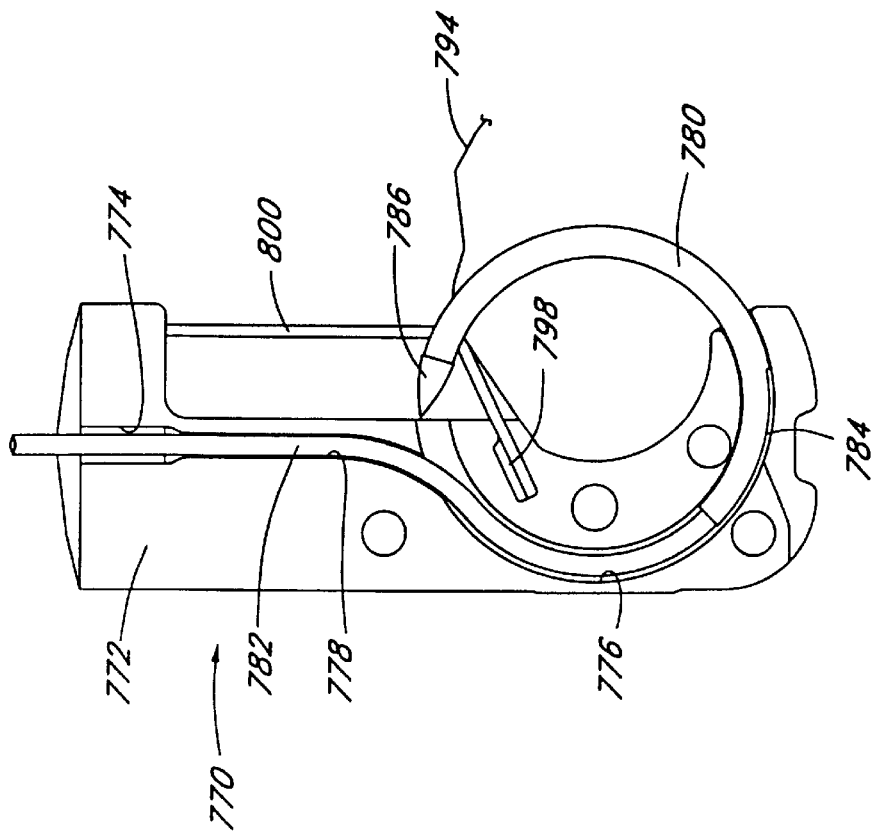
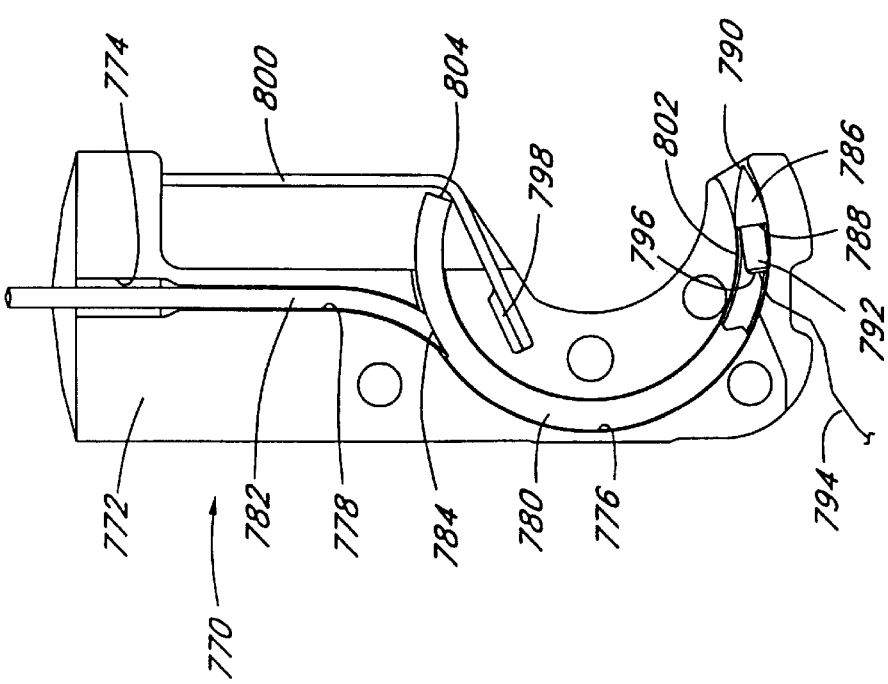

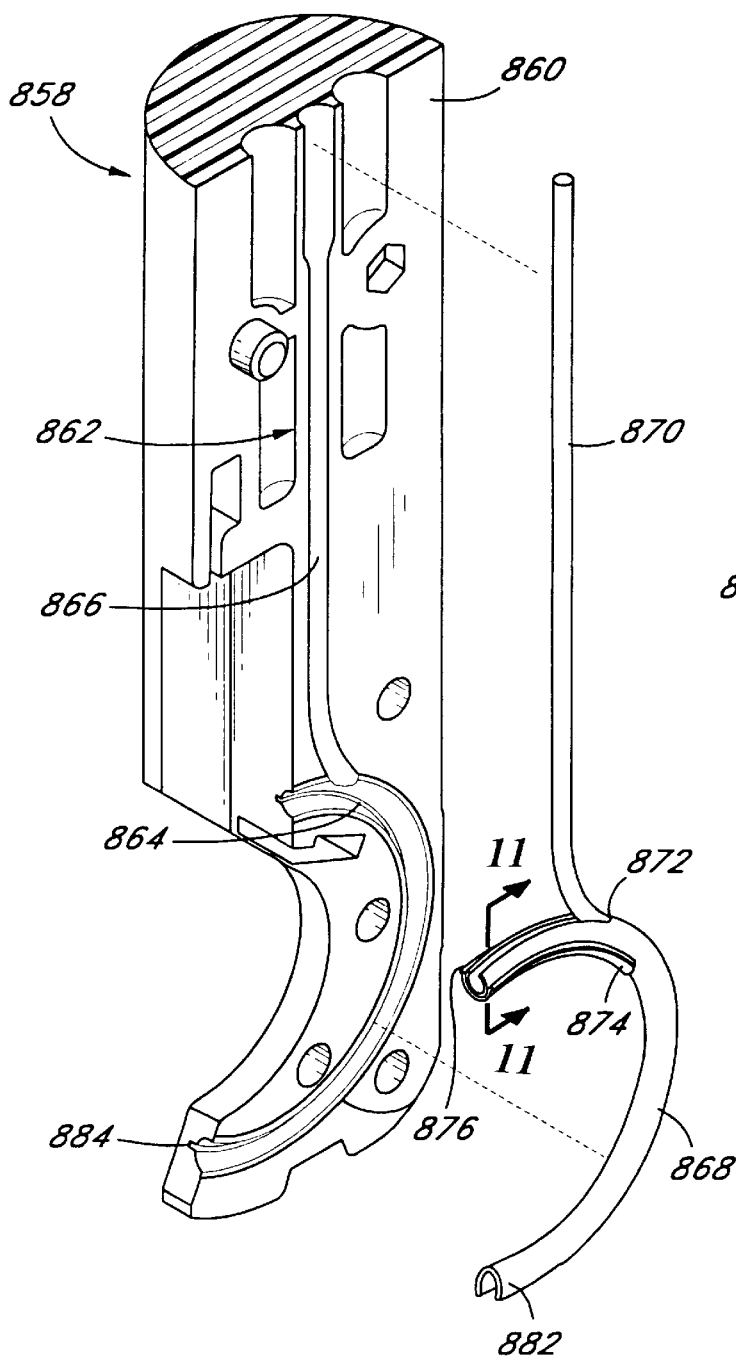
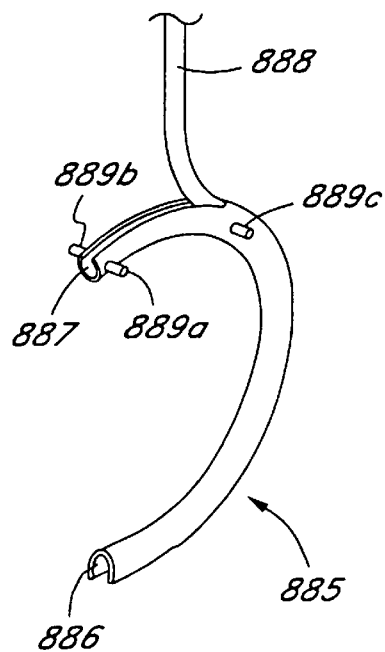

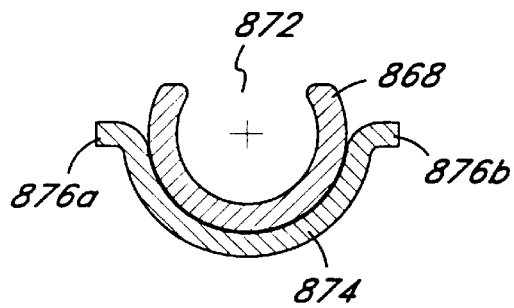
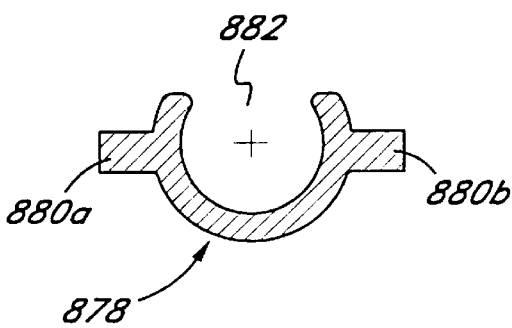
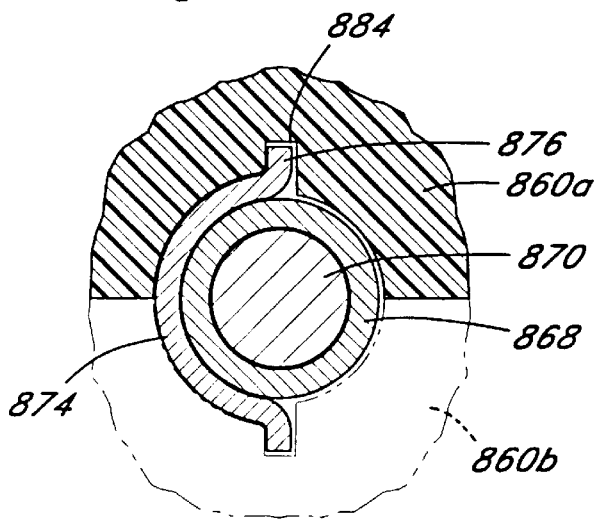
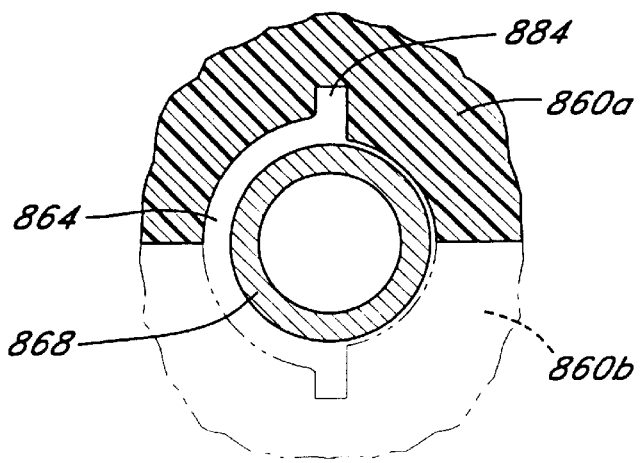

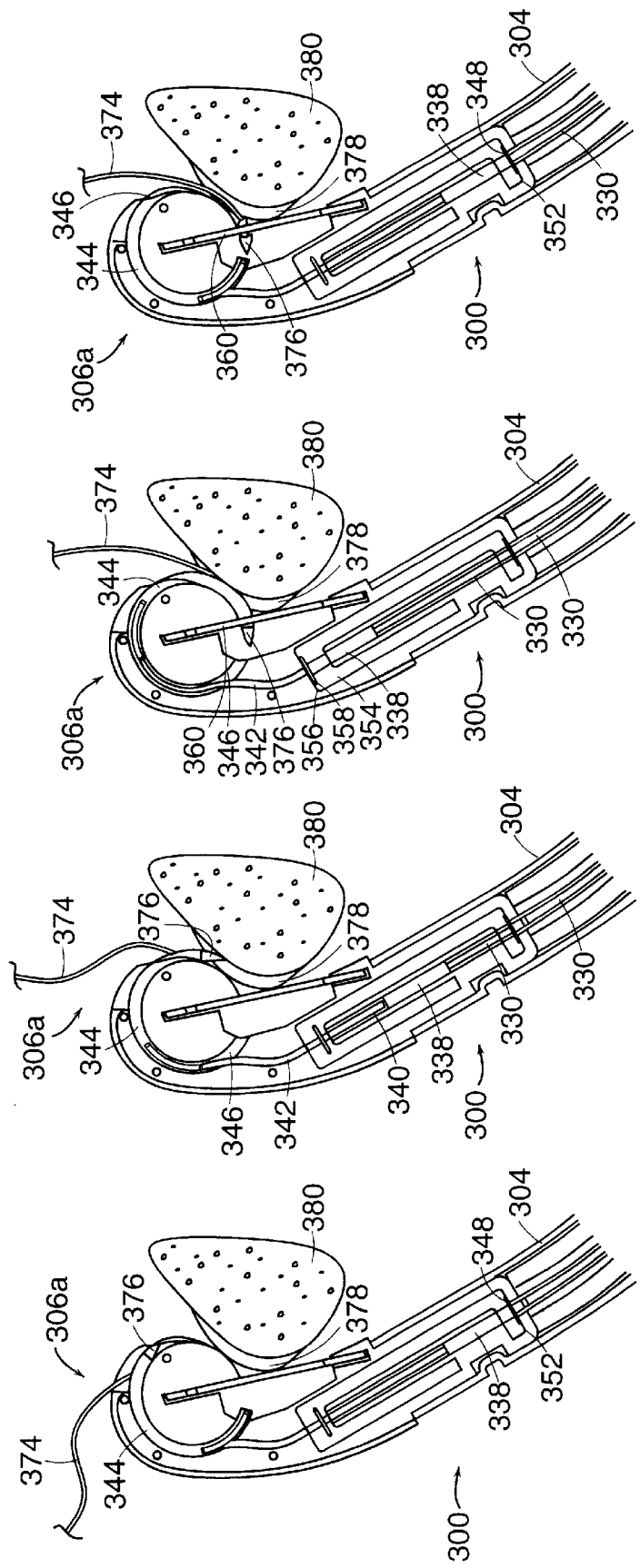

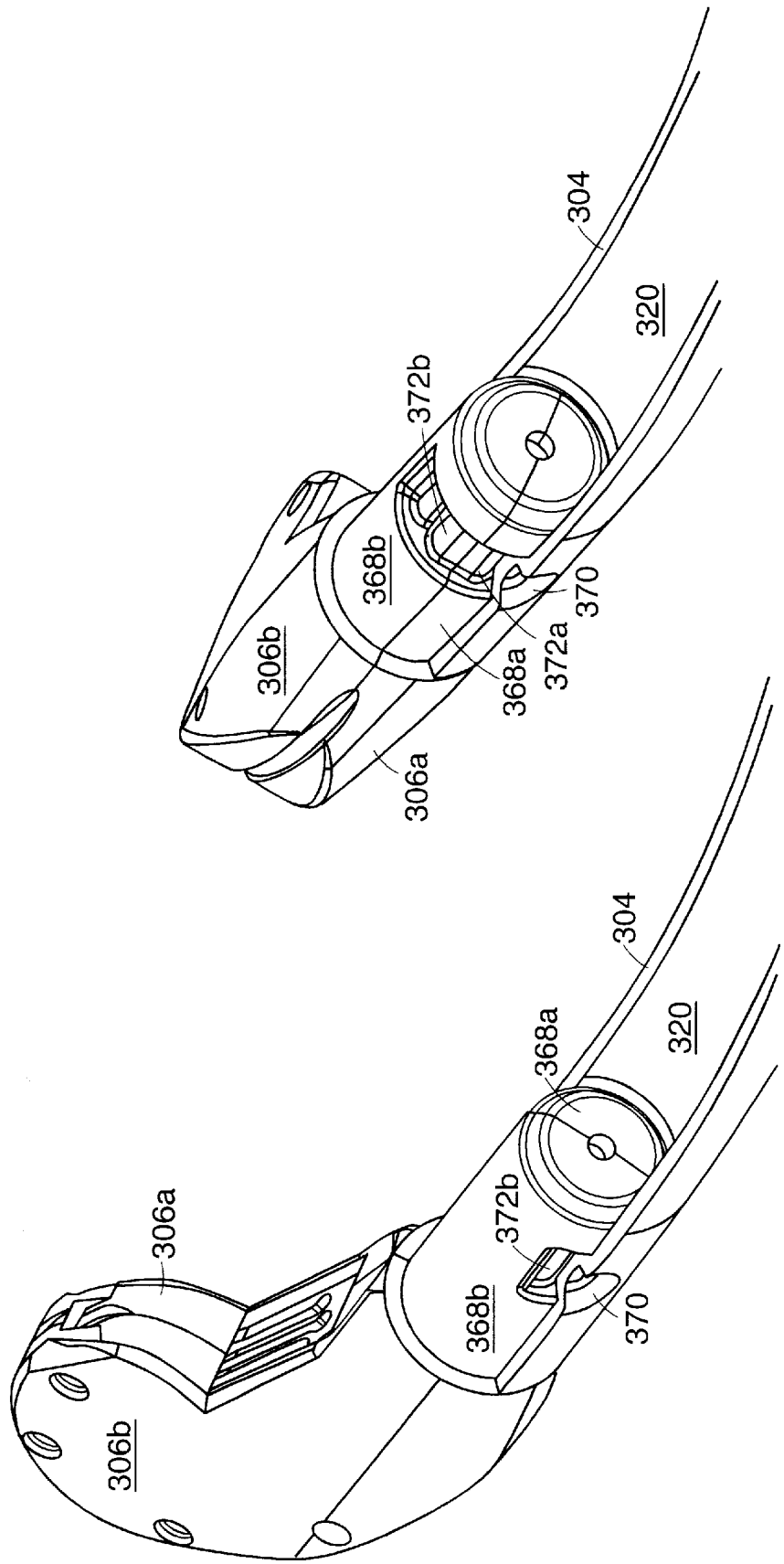

TRANSVAGINAL SUTURING SYSTEM

RELATED APPLICATIONS

This patent application is a continuation-in-part of patent application Ser. No. 09/002,875 filed Jan. 5, 1998, now abandoned, by inventors Norman S. Gordon, Robert P. Cooper and Richard L. Quick, and entitled "Needle Guidance System for Endoscopic Suture Device"; which is a continuation of patent application Ser. No. 08/554,743 filed Nov. 7, 1995, now U.S. Pat. No. 5,713,910, by inventors Norman S. Gordon, Robert P. Cooper and Richard L. Quick, and entitled "Needle Guidance System for Endoscopic Suture Device"; which is a continuation-in-part of patent application Ser. No. 08/311,967, filed Sep. 26, 1994, now U.S. Pat. No. 5,578,044, by inventors Norman S. Gordon and Robert P. Cooper, and entitled "Endoscopic Suture System"; which is a continuation-in-part of patent application Ser. No. 08/205,042, filed Mar. 2, 1994, now U.S. Pat. No. 5,540,704, by inventors Norman S. Gordon, Robert P. Cooper and Gordon C. Gunn, and entitled "Endoscopic Suture System"; which is a continuation-in-part of patent application Ser. No. 08/057,699, now U.S. Pat. No. 5,458,609, filed May 4, 1993, by inventors Norman S. Gordon, Robert P. Cooper and Richard L. Quick, and entitled "Endoscopic Suture System"; which is a continuation-in-part of patent application Ser. No. 07/941,382, filed Sep. 4, 1992, now U.S. Pat. No. 5,364,408, by inventor Norman S. Gordon, and entitled "Endoscopic Suture System". The entirety of each of the above referenced patent applications is hereby incorporated herein by reference.

FIELD OF THE INVENTION

The invention relates to devices for approximation, ligation and fixation of tissue using a suture, to various constituent parts comprising said devices, and particularly to the placement of sutures into certain difficult to access ligamental structures, to the approximation of tissue separated by means of an endosurgical trocar being inserted into a body cavity, and to approximation, ligation, and fixation of body tissue using both traditional open surgical and endosurgical techniques and instruments.

BACKGROUND OF THE INVENTION

Suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle carrying suture through body tissues to approximate, ligate and fixate them. Many prior disclosures, such as described in Drake et al, U.S. Pat. No. 919,138 issued Apr. 20, 1909, employ a hollow needle driven through the tissue with the suture material passing through the hollow center lumen. The needle is withdrawn leaving the suture material in place, and the suture is tied, completing the approximation. A limitation of these types of devices is that they are particularly adapted for use in open surgical procedures where there is room for the surgeon to manipulate the instrument.

Others have attempted to devise suturing instruments that resemble traditional forceps, such as Bassett, U.S. Pat. No. 3,946,740 issued Mar. 30, 1976. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

The term "endosurgery" means endoscopic surgery or surgery performed using an endoscope. In conjunction with a video monitor, the endoscope becomes the surgeons' new eyes from which they operate. Operations using an endoscope are significantly less invasive when compared to traditional open surgery. Patients usually return home the next day or in some cases the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes. Such an instrument is disclosed by Mulhollan et al, U.S. Pat. No. 4,621,640 issued Nov. 10, 1986. Mulhollan describes an instrument that may be used to hold and drive a needle, but makes no provision for retrieval of the needle from the body cavity, nor the completion of the suture by tying. Mulhollan's instrument is limited in that the arc through which the needle must be driven is perpendicular to the axis of the device. Another such instrument intended for endoscopic use is described by Yoon, U.S. Pat. No. 4,935,027, issued Jun. 19, 1990. This instrument uses oppositional hollow needles or tracks pushed through the tissue and coapted to create a tract through which the suture material is pushed. It is not clear how these curved tracks would be adapted to both be able to pierce the tissue planes illustrated, parallel to the tips of the tracks, and be curved toward each other to form the hollow tract.

The invention herein described may be used for final closure of umbilical and secondary trocar puncture wounds in abdominal tissues including the fascia and other layers. The umbilical puncture is routinely a puncture site of 10 mm to 12 mm. Future procedures may require trocar puncture sites up to 18 mm and greater in size. Due to the large size of the puncture wound, it is important that the site be closed or approximated at the interior abdominal wall following removal of the large trocar cannula. An improper or non-existent closure can lead to a herniation of the bowel and/or bowel obstruction. The present mode for closure is to reach down to the desired tissue layer with a pair of needle drivers holding a needle and suture material and secure a stitch. Many patients are obese and present considerable fat in this region. Because the abdominal wall may be several inches thick, it is extremely difficult, tedious and time consuming to approximate the fascial tissues with a suture. Often times, following removal of a large trocar, the puncture site needs to be enlarged to accomplish this, thus negating some of the advantages of endoscopic surgery previously discussed.

One of the embodiments described herein may be of particular advantage in performing a surgery for correction of female stress incontinence, which affects over 5 million women in the United States. Stress incontinence is caused when the structures defining the pelvic floor are altered by aging or disturbed by the process of childbirth or other trauma. These structures in the pelvic floor normally hold the urinary bladder such that maintenance of a volume of urine in the bladder is accomplished by a combination of muscle tone and bladder positioning.

There are a number of surgical procedures that may be performed in order to restore the normal anatomical position of the urinary bladder. The classic open Burch suspension procedure is one such procedure and is a straightforward surgical treatment for correction of female stress incontinence. During this procedure, sutures are precisely placed in the wall of the vagina on each side of the urethra, with care being taken to avoid puncturing either the urethra or the mucosal layer of the vagina. These sutures are then looped through a ligament, called Cooper's ligament, which runs along the posterior ridge of the pubic bone. These sutures are then pulled taut, and carefully tied to suspend the urinary bladder in a more anatomically sound position, restoring normal urinary function and continence.

One of the problems with the procedure described above is that it is normally done only in conjunction with other scheduled abdominal surgical procedures such as a hysterectomy. This is because, as described earlier, an open surgical approach requiring a large abdominal incision must be used, and it is not very common for a patient to elect to have a major abdominal surgical procedure just for the treatment of incontinence.

Consequently, of late, new approaches to the performance of the classical open Burch procedure have been attempted. One approach is a procedure known as a laparoscopic Burch suspension procedure, and has begun to find favor among physicians. Another approach that has shown great promise is a transvaginal approach for the placement of the sutures.

The laparoscopic approach to the Burch procedure has all of the advantages of laparoscopy described earlier with respect to post operative pain, hospital stay and recovery time. There are three difficulties associated with the laparoscopic approach; access, suture placement, and knot tying. The present invention addresses the problems surrounding the placement of the sutures in the appropriate structures and in the optimal position, and also addresses particular aspects of needle retrieval and knot tying when using endoscopic techniques.

Currently, the placement of sutures while using endoscopic techniques involves placing a semi-circular needle, attached to and carrying a suture, in a pair of endoscopic needle holders. These needle holders, which resemble a pair of pliers with an elongated shaft between the handles and the jaws, must be placed down through one of the surgical trocars into the body cavity containing the structure to be sutured. Because of their size, the needles used in these procedures are generally not able to be held in the jaws of the needle driver while being introduced through the operative trocar. The surgeon must hold the suture string in the needle holder jaws, and push the needle holder trailing the needle and suture into the body cavity. The suture and needle combination is dropped in the body cavity, and the needle is then located and picked up and properly positioned in the needle holder jaws. This is a difficult and time-consuming aspect of the current endoscopic technique for suturing. The needle carrying the suture may then be driven by pronation of the wrist, causing rotation of the elongate shaft, and subsequent arcuate rotation of the semi-circular needle.

It may be seen that a limitation of this type of needle driver is that the needle may only be driven or rotated in a plane perpendicular to the axis of rotation, such axis being described by the elongate shaft and the position of the surgical trocar. Thus the current endoscopic needle drivers will not allow the surgeon to swing the needle in an arc parallel to the trocar's axis. This is a severe limitation in the case of the laparoscopic Burch, because of the orientation of the anatomy relative to the planes of access. The vaginal wall and the Cooper's ligament require the sutures to be placed in a orientation that makes the procedure extremely difficult and time consuming with the use of currently available instrumentation. It is also a limitation when attempting to ligate vessels, ligaments and other structures that run perpendicular to the axis of the operative trocar.

Another limitation of the current instrumentation is seen in the aspect that requires the surgeon to prepare the needle for penetration of the tissue while the needle is inside the body. This process is a time consuming, and sometimes frustrating exercise in hand to eye coordination, which is complicated by the fact that the surgeon is viewing the three dimensional space inside the body cavity through a two dimensional video monitor.

It may also be seen that the surgeon must be able to retrieve the needle trailing the suture material back through the same surgical trocar through which the needle driver is placed. This allows a knot to be tied in the suture outside of the body, and pushed down the trocar to the structure being sutured. Thus the needle driver must be able to retrieve the needle and bring the needle trailing the suture back up through the same trocar through which it is introduced allowing the tied knot to be pushed back down into the operative site.

It may also be seen that if the surgeon desires to place more than one suture throw through the tissue, he must be able to reload the needle into the needle driver. This may be done extracorporeally, that is, outside the body, in a manner similar to the initial loading of the suture device, or it may be done intracorporeally, that is, inside the body. Features which facilitate the intracorporeal loading of the needle can be seen to provide the surgeon with another option in the application of suture material to tissues, and could save operative time.

While laparoscopy has certainly found favor with many physicians as an alternative operative modality, the advanced skill set and operative time necessary to become an efficient and practiced laparoscopist have proven to be a challenge for a large portion of the surgical community. The cost pressures brought about by large scale patient management (the continued rise and success of health maintenance organizations or HMO's) have also made the surgical community to cast a critical eye on the overall costs and long-term outcomes of some of the procedures that have been tried via a laparoscopic approach. While the laparoscopic cholecystectomy (gall bladder removal) has certainly proven its worth in the past 8–10 years, many other procedures have not shown similar cost effectiveness and positive long-term outcomes.

Hence, alternatives have been sought to bridge the gap between skill and equipment intensive laparoscopic surgery and more familiar open surgery. As such, under the broad umbrella of "minimally invasive surgery" which would include laparoscopic surgery, a relatively new approach called "mini-incision surgery" has begun to emerge. This approach uses the principles of traditional open surgery, along with some of the equipment advances of laparoscopy to provide the patient with the best of both worlds.

Perhaps the most visible of these new approaches is the emergence of minimally invasive heart surgery, both for coronary bypass and for valve replacement. Techniques and tools for cardiovascular surgery have begun to be used that allow the heart surgeon to perform procedures through small incisions between the ribs that previously required a massive incision and splitting the sternum to gain access to the heart.

In a similar way, gynecologists have begun to explore alternatives to the traditional open abdominal approach for the many indications requiring reconstruction of some aspect of the pelvic floor, such indications including genuine stress incontinence, vaginal prolapse, cystocele, rectocele, and enterocele.

There have been described in the literature many transvaginal approaches to the treatment of urinary stress incontinence. This includes procedures described by Pereyra, Raz, and Stamey. Pereyra originally described his approach in 1959, with modifications to improve results and reduce complications described in 1967, 1978, and 1982. Raz disclosed his approach in 1981, and Stamey in 1973. These procedures were developed with the goal of combining the good results of a suprapubic colposuspension (for example, the above-described Burch procedure) with a vaginal repair that leaves the abdominal wall intact.

These procedures have some common elements; they all place sutures in the vaginal wall at the urethral-vesical junction (the bladder neck), and use some form of attachment to the abdominal wall for the suspension. This attachment is somewhat problematic in that the abdominal wall moves when the patient tenses or relaxes the stomach muscles. This in turn moves the bladder neck, and sometimes results in loss of urine (hence continued incontinence), or results in the opposite problem, an inability to void due to the bladder neck being kinked. The reason for the attachment to the movable abdominal wall instead of to the fixed Cooper's ligament is that the Cooper's ligament is all but impossible to reach with current instrumentation via a transvaginal approach.

It should be noted that although these procedures are easier to perform than the suprapubic approaches, and result in less post operative recovery time for the patient, the long-term continence rates have 15–30% below those for the suprapubic approaches. Thus it is clear that if one could attach the sutures to the fixed Cooper's ligament via a transvaginal approach, the best aspects of both procedures may be realized; the short recovery times of the transvaginal approach and the good long term continence results of the suprapubic approach.

As it will be obvious to those skilled in the art, the use of the techniques described above for the performance of the Burch bladder suspension procedure may be used for other suturing tasks, such as for ligating vessels and ligaments during the performance of, for example, a hysterectomy or oophorectomy, or for the approximation of tissue flaps such as in the performance of procedures, for example, for the treatment of gastro-esophageal reflux disorder.

Currently, a number of manufacturers of suture materials and needles exist. There are USP (United States Pharmacopeia) standards for the suture material diameters and tensile strengths, however no similar standards exist for the suture needles. There are however, conventional "standard" needle sizes that many manufacturers fabricate. The needles are generally specified by the needle wire diameter, needle length and the bend arc length. A common needle size for most suture manufacturers, for example, is 26 mm long by ½ arc (180°). As it may be seen by geometric construction, a 26 mm×180° needle describes a fixed bend radius, and this nominal bend radius is fairly consistent from manufacturer to manufacturer. Typically, the suture material is crimped in either a U shaped channel formed in the distal portion of the needle, or in a drilled hole. The crimp zone size and configuration varies between manufacturers, and generally tends to straighten out the bend radius in that localized area. Between the manufacturing tolerances in the bend radius and the straightening of the end of the needle in the crimp zone, the repeatability of the shape of the needle and suture combination may vary significantly. It is therefore desirable to construct an needle guide channel which will both guide the needle precisely, and allow for the aforementioned manufacturing tolerances and perturbations. This would allow readily available commercial suture and needle combinations to be used with the suture placement system.

None of the prior art devices are adaptable to effect the placement of a suture in the anterior abdominal wall, nor are they adaptable to place sutures precisely and controllably while making provision for needle retrieval when using endoscopic techniques. None of the prior art devices make it possible to place sutures into Cooper's ligament via a transvaginal approach. It is therefore an object of the present invention to provide a family of novel suturing devices that overcomes the above set out disadvantages of prior known devices in a simple and economical manner.

It is a further object of the present invention to provide a suture device that will permit the approximation of the separated edges of a puncture wound without making a larger incision to expose the wound margins.

A further object of the present invention is to provide a suture device that will permit the surgeon to apply substantial force to the needle, permitting it to be driven through tough tissues, for example, a ligament or the abdominal fascia.

It is a further object of the present invention to provide a suture device that can be used in conjunction with modern day endoscopic surgical techniques.

Another object of the invention is to provide a suture device that will allow a needle to be driven in an arc which describes a plane parallel to the axis of the device.

Yet another object of the invention is to provide a suture device that may be used to approximate the edges of an internal wound. Another object of the present invention is to provide a suture device that permits the penetration of two needles having suture material extending there between into and through the sides of a wound and into catches thereby creating a suture loop through the wound that may be tied to approximate the tissues.

Another object of the invention is to provide a suture device that will permit the surgeon to place sutures around vessels, ligaments, and other structures to effect ligation.

It is a further object of the present invention to provide a suture device that will permit the surgeon to place sutures in the Cooper's ligament by palpation via a transvaginal approach.

SUMMARY OF THE INVENTION

The present invention is a new medical device that allows the surgeon to quickly and easily place a suture in the interior wall of a body cavity to approximate the tissues separated as a result of a puncture wound made by the introduction of a surgical trocar into a body cavity during endoscopic surgery. The invention described herein may also be used to approximate the margins of an open wound in an internal organ, such as the uterus or the stomach, such as would be effected during the course of a resection for benign or malignant lesions, and may also be used for placing sutures into Cooper's ligament or other structures via a transvaginal approach. The transvaginal approach to the classic open Burch (the open Burch being acknowledged as the gold standard treatment for genuine urinary stress incontinence) is a new and novel procedure that has become possible due to the specific design aspects of the present invention.

One embodiment of the present invention includes needle holders that releasably hold a pair of needles that are in turn attached to each end of a single piece of suture material. Such needle holders are held within tubular guiding tracks housed within a hollow outer sleeve that may be introduced into a puncture wound. The needle holders and guiding tracks may be deployed outside the hollow sleeve to allow the needles to engage the tissue to be approximated. A plunger is coupled to rigid driving members that are in turn attached to flexible driving members adapted to follow the shape of the guiding tracks. The flexible driving members are suitably attached to the needle holders. The plunger is pushed, simultaneously driving the needle pair into opposite sides of the puncture wound and into catches also disposed within the hollow sleeve. The needle holders are retracted into the guiding tracks, and the tracks pulled back into the hollow sleeve trailing the suture material. The device may then be withdrawn, leaving a loop of suture material precisely placed in the selected tissue, for example, in the interior wall of the body cavity. The needles are removed from the ends of the suture, and the suture material is tied to complete the approximation of the tissue.

In one aspect, the present invention differs from the prior art in that it allows a suture to be placed in a retrograde fashion in the puncture wounds created during the introduction of trocars used for endoscopic surgery. These puncture wounds have margins perpendicular to the plane of tissue dissection, unlike the wounds that are addressed by prior art in which the tissues generally overlap. Presently, all the existing instruments are designed to either approximate tissues to which direct visual and physical access may be gained during open surgery, or to approximate tissues that may be pinched between the jaws of a forceps like instrument. Wounds in body organs such as the uterus or the stomach which are created during the resection or removal of benign or malignant lesions may also have wound margins which require end to end approximation instead of overlapping. The present invention allows the surgeon to independently pass a needle through each side of the wound to allow the two sides to be drawn together, approximating the tissue.

The needle driver apparatus of the present invention may be constructed in a number of different ways. Several of the preferred ways are described herein. One embodiment uses needle guides which are semicircular in shape, holding either a semicircular needle, or a semicircular needle holder with a small needle tip. These guides are disposed across their diameter within a hollow tubular sleeve when in the retracted mode, and are rotated about one end to deploy them outside the bounds of the hollow sleeve for engaging the tissue to be sutured. The needles, or the needle holders, are driven through the tissue by axial movement of a rigid cylindrical member which contacts a flexible cylindrical member that follows the semicircular shape of the guide tracks. The needles are caught in catches placed within the hollow tubular sleeve that capture the needle by means of a leaf spring disposed to flex, preferably in one direction, and squeezing into grooves or recesses in the needles, thereby retaining the needles to the hollow tubular sleeve. The needle guides may be retracted, and the instrument removed from the wound, thus trailing the suture material. The needles are removed, the suture is tied, and the approximation is completed.

Another version of the device uses semicircular needle holders similar to the previous version, but the needle guides are eliminated. The needle holders are instead rotated about their axes such that the needles attached to the ends of the holders describe an arc that encompasses the tissue to be sutured.

It is contemplated that the above embodiments may be modified to include needle paths other than circular, such as helical, elliptical or straight, by modification of the needles, the needle holders and the needle guides. It is also possible to adapt the above configurations to allow each of the needles to be actuated and driven independently by dividing the deployment controls and the needle drivers into separate left and right hand members. Further, it is possible to utilize a tool that uses only a single needle and guides it through both sides of the wound as opposed to the double needle configuration described above.

Accordingly, another embodiment of the device uses a single needle which eliminates the deployment aspect of the needle guides. The needle guide track is incorporated directly into the cannular body which is particularly adapted for use in endoscopic procedures. The cannular -body is of a diameter such that it may be placed through, for example, a standard 10 mm–12 mm trocar. The needle may be a long shouldered needle such as described previously, or may be a standard ½ circle, or 180° needle, with a length of, for example, 22 to 28 mm and crimped onto a length of standard suture material. As previously discussed, those skilled in the art will understand that various needle wire diameters, needle bend radii, needle cross sections, and suture materials are all adaptable to be used in the devices described herein. The needle may be loaded into the preformed needle guide track in the cannular body. It should be noted that the needle is placed in the cannular body across its diameter such that the point of the needle lies substantially perpendicular to the axis of the cannular body. As in previous embodiments, axial movement of a flexible drive member drives the needle out of the guiding track into and through tissue placed adjacent to the exit opening in the cannular member.

After having driven the needle into tissue, if the needle is a shouldered needle, it may be retrieved by using a keyhole shaped slot incorporated into the side of the cannular body. If the needle is a standard, non-shouldered needle, standard laparoscopic graspers, which have been introduced into the operative site via a secondary trocar, may be used to pull the needle up a short distance trailing the suture. The needle driver may then be used to retrieve the needle and suture combination by either pinching the suture material in a groove fashioned for that objective, or clamping the needle with a means adapted for that purpose. The needle trailing the suture may then be withdrawn through the surgical trocar.

This basic method of driving and retrieving the needle may be used in a number of ways at the surgeon's discretion to effect approximation, ligation, or fixation of tissue.

Approximation involves the placement of one to multiple sutures in order to pull the edges of a wound together to effect healing. Ligation involves placing a suture circumferentially about a vessel or duct in order to tie it off. In the case of ligation, only a single suture is placed, and a knot tied to strangulate the encompassed structure. Fixation involves the placement of sutures to positionally secure tissues in a particular orientation, and may require that multiple sutures be placed. Fixation may also require that each end of the suture be driven through the tissue more than once.

As it may be apparent, provisions for needle retrieval, the capability of the needle to be reloaded into the needle guide track, and the positioning and orientation of the needle are often desirable features, making it possible to efficiently and effectively place sutures for various therapeutic reasons. The invention herein described solves these problems.

The above described embodiments may be modified to include a needle carrier adapted as described before to hold a short barbed needle. This carrier may be disposed within the preformed needle guide track in the cannular body. A similar catch mechanism as described previously is incorporated into the side of the cannular body at the end of the arcuate path described by the short needle/needle carrier combination when axial movement of the flexible drive member drives the needle and carrier combination out of the guide and through the tissue to be sutured. Use of this embodiment for closure of trocar puncture wounds can be accomplished by loading one end of a suture prepared with short needles at both ends into the needle carrier. The instrument is inserted into the puncture wound by means of the trocar placed therein. The instrument is located such that the tip of the needle is placed directly against the inside of the abdominal wall.

The needle is driven up into the abdominal fascia by the flexible needle driver coupled to the needle driver button, and into the catch. The short needle stays in the catch, the needle carrier is withdrawn back into the needle guide track, and the entire device is withdrawn from the surgical trocar. The needle is removed from the catch, the opposite end of the suture with its attached short needle is loaded into the instrument, and the entire process is repeated with the second end of the suture being driven into the tissue on the opposite side of the puncture wound, 180° from the initial stitch. The instrument and trocar are removed from the wound, and the remaining loop of suture is tied to approximate the tissues, thus closing the wound.

As it may be appreciated, this embodiment may be used in order to effect suturing in many different parts of the body, and is not limited to the closure of the wounds caused by the insertion of operative trocars into a body cavity. With the availability of both absorbable and non-absorbable suture material attached to the short needles, it is contemplated that the above described embodiment may be used in performance of procedures such as, for example, the laparoscopic Burch previously described. It is also contemplated that ligation of vessels and ligaments, such as, for instance, the ligation of uterine vessels and ligaments during the performance of a hysterectomy may be accomplished with this embodiment. This embodiment may also find application in the repair of the meniscal tissue in the knee or shoulder. It is to be clearly understood that this embodiment eliminates the manual step of needle retrieval from the wound, as the needle is automatically captured by the instrument itself.

Another embodiment of the device, which may be seen to incorporate many of the above-described features, is particularly adapted for the placement of sutures into the Cooper's ligament via a transvaginal approach. These features include the design and functional aspects of the needle carrier, the short barbed or shouldered needle carrying the suture and the needle catch. This embodiment includes additional adaptations of the elongate body and an additional degree of freedom for articulation of the head of the device.

Due to the anatomical placement of the Cooper's ligament bilaterally on the inferior aspect of the pubic ramus, it is necessary for this embodiment of the device to have a curved elongate body to allow for placement of the device head against the superior aspect of the ramus through an incision in the vaginal wall (a colpotomy). This device also has allowance for the head of the instrument, with the needle carrier and catch, to be rotated axially left or right to an angle of, for example, 45° to accommodate the pubic arch.

The head of the device also incorporates a unique design for controlling the depth of penetration of the needle and needle carrier combination in order to place the suture material consistently into the ligament without penetrating the pubic bone. This is important because the Cooper's ligament lies directly on the pubic bone, and penetration of the bone by the needle during the placement of the suture may cause osteitis pubis (bone infection).

The method of use of this device is as follows: an incision is made bilaterally in the anterior vaginal wall, just lateral to the bladder neck. The space of Retzius is dissected by sweeping the surgeon's finger along the inferior aspect of the pubic ramus, from the symphysis pubis out as far laterally as can be reached, preferably as far as the obturator fossa. The Cooper's ligament may be palpated, and using the symphysis as the medial landmark, and the obturator fossa as the lateral landmark, the instrument is guided by palpation up onto the superior aspect of the pubic ramus. A notch in the face of the head of the device is provided to allow the instrument to be accurately placed for delivery of the suture through Cooper's ligament.

After proper positioning of the instrument is verified, the needle driver button is pushed, driving the needle carrier and needle suture combination through the ligament and into the needle catch. The shouldered needle is captured in the needle catch, and the needle carrier is retracted back into the device head. The entire device is withdrawn through the colpotomy, trailing the suture. A second pass through the ligament is optional. The free ends of the suture are then passed through the vaginal mucosa, and tied with a pulley stitch to allow for proper positioning of the bladder neck. The procedure is repeated on the contralateral side, both pulley stitches tied to the appropriate tension to effect the bladder neck suspension, and the colpotomy closed with absorbable suture.

It may be seen that for an instrument to automatically capture a needle in a consistent and repeatable fashion, it is important that the needle be guided into the catching mechanism in a predictable way. This will allow the catch to function properly, and reduces the possibility that the needle would not be engaged in the catch after being driven through tissue. It is also important that the needle drive mechanism operates with as little friction as possible, in order to allow the surgeon to have some tactile sense of the tissue being sutured.

It may also be appreciated that the limitations of the angles of access and the restrictions on the lateral manipulation of instruments used during endoscopic procedures imposed by the operative trocars can make reaching certain anatomical structures difficult. Thus, the ability to articulate an instrument within the body cavity independent of the manipulation of the main body shaft can be of particular advantage in accessing these difficult to reach structures. By articulating the head of the needle driver instrument, the exit angle of the needle may be adjusted, as well as opening the possibility of accessing certain areas of the body which are inaccessible in a linear fashion due to the aforementioned mechanical constraints.

In a first aspect, the present invention is a suturing instrument comprising: an elongate body member having a longitudinal axis; a suture deployment system located within a distal end portion of the elongate body member wherein the distal end portion includes a suture exit port, the suture deployment system comprising: a curved suture carrier channel; and a curved suture carrier movably positioned in the curved suture carrier channel; and a deployment controller having a proximal end, a distal end, a retracted position and a deployed position, the deployment controller extending substantially along the longitudinal axis of the elongate body member to the distal end of the elongate body member where it is coupled to the curved suture carrier and moves the curved suture carrier through the curved suture carrier channel as it moves between the retracted position and the deployed position, the curved suture carrier channel configured within the distal end portion of the elongate body member such that the curved suture carrier exits the suture exit port and is guided along a path which includes a proximal curved path segment such that a surface of the curved suture carrier is substantially adjacent with an outer surface of the distal end portion of the elongate body member along the proximal curved path segment. The suturing instrument may further include a suture catch positioned proximate to the distal end portion of the elongate body member such that a distal path segment of the curved suture carrier path is intercepted by the suture catch as the deployment controller approaches the deployed position. The suturing instrument further include a surgical needle positioned in a distal end of the curved suture carrier. In some devices, the surgical needle further comprises a bullet needle. In other aspects, the curved suture carrier channel and the curved suture carrier are located in a distal tip assembly of the elongate body member; and the distal tip assembly is joined with the elongate body member such that the distal tip assembly is free to rotate axially about the elongate body member longitudinal axis. Another aspect of the device has the deployment controller coupled to the curved suture carrier with a flexible driver member. This flexible driver member may further comprise an alloy of nickel and titanium.

In a second aspect, the present invention is a suturing instrument comprising: a body member; a suture exit port formed in the body member; a curved suture carrier channel formed in the body member; and a curved suture carrier movably positioned in the curved suture carrier channel, wherein the curved suture carrier has a retracted position such that the curved suture carrier is positioned within an interior region of the body member and a deployed position such that a portion of the curved suture carrier is positioned exterior to the body member, the curved suture carrier configured within the curved suture carrier channel such that the curved suture carrier exits the interior region of the body member through the suture exit port and is guided along a path which includes a proximal curved path segment wherein a surface of the curved suture carrier is substantially adjacent with an outer surface of the body member along the proximal curved path segment. This device may further include a suture catch positioned on the body member such that a distal path segment of the curved suture carrier path is intercepted by the suture catch. This instrument may also include a surgical needle positioned in a distal end of the curved suture carrier. The surgical needle may further comprise a bullet needle.

In a third aspect, the present invention is a suturing instrument comprising: an elongate body member having a longitudinal axis; a distal tip suture deployment assembly joined with a distal end of the elongate body member such that the distal tip assembly is free to rotate axially about the elongate body member longitudinal axis, the distal tip suture deployment assembly comprising: a distal tip body member; a suture exit port formed in the distal tip body member; a curved suture carrier channel formed in the distal tip body member; and a curved suture carrier movably positioned in the curved suture carrier channel; and a deployment controller having a proximal end, a distal end, a retracted position and a deployed position, the deployment controller extending substantially along the longitudinal axis of the elongate body member to the distal end of the elongate body member where it is coupled to the distal tip suture deployment assembly and moves the curved suture carrier through the curved suture carrier channel as it moves between the retracted position and the deployed position. In this device, the distal tip suture deployment assembly may be configured to have a retracted position such that the curved suture carrier is positioned within an interior region of the distal tip body member and a deployed position where a portion of the curved suture carrier is positioned exterior to the distal tip body member, the curved suture carrier configured within the curved suture carrier channel such that the curved suture carrier exits the interior region of the distal tip body member through the suture exit port and is guided along a path which includes a proximal curved path segment wherein a surface of the curved suture carrier is substantially adjacent with an outer surface of the distal tip body member along the proximal curved path segment. This device may further comprise a suture catch positioned on the distal tip body member such that a distal path segment of the curved suture carrier path is intercepted by the suture catch as the deployment controller approaches the deployed position. The instrument may further comprise a surgical needle positioned in the distal end of the curved suture carrier. In some aspects, the surgical needle may be bullet needle.

In a fourth aspect, the present invention is a method for placing a suture in thin tissue adjacent bone structure comprising: placing a suturing instrument which encloses a curved suture carrier which is movably positioned within a curved suture carrier channel adjacent the tissue to be sutured; and deploying the curved suture carrier out of the suturing instrument through an exit port such that the curved suture carrier exits an interior region of the suturing instrument through the exit port along a path which approaches being substantially tangential to an outer surface of the suturing instrument surrounding the exit port.

In a fifth aspect, the present invention is a suturing instrument comprising: a body member; an exit port formed in the body member; a curved suture carrier channel formed in the body member; and a curved suture carrier movably positioned in the curved suture carrier channel, wherein the curved suture carrier has a retracted position such that the curved suture carrier is positioned within an interior region of the body member and a deployed position such that a portion of the curved suture carrier is positioned exterior to the body member, the curved suture carrier configured within the curved suture carrier channel such that the curved suture carrier exits the interior region of the body member through the exit port along a path which approaches being substantially tangential to an outer surface of the body member surrounding the exit port.

In a sixth aspect, the present invention is a suturing instrument comprising: an elongate body member having a longitudinal axis; a suture deployment system located within a distal end portion of the elongate body member wherein the distal end portion includes a suture exit port, the suture deployment system comprising: a curved suture carrier channel; and a curved suture carrier movably positioned in the curved suture carrier channel; and a deployment controller having a proximal end, a distal end, a retracted position and a deployed position, the deployment controller extending substantially along the longitudinal axis of the elongate body member to the distal end of the elongate body member where it is coupled to the curved suture carrier and moves the curved suture carrier through the curved suture carrier channel as it moves between the retracted position and the deployed position, the curved suture carrier channel configured within the distal end portion of the elongate body member such that the curved suture carrier exits the suture exit port along a path which approaches being substantially tangential to an outer surface of the body member surrounding the suture exit port. This aspect of the invention may further comprise a suture catch positioned proximate to the distal end portion of the elongate body member such that a distal path segment of the curved suture carrier path is intercepted by the suture catch as the deployment controller approaches the deployed position. A surgical needle may be positioned in a distal end of the curved suture carrier. The surgical needle may further comprise a bullet needle. Additionally, the curved suture carrier channel and the curved suture carrier may be located in a distal tip assembly of the elongate body member; and the distal tip assembly is joined with the elongate body member such that the distal tip assembly is free to rotate axially about the elongate body member longitudinal axis. The deployment controller may be coupled to the curved suture carrier with a flexible driver member. The flexible driver member may further comprise an alloy of nickel and titanium.

These and other characteristics of the present invention will become apparent through reference to the following detailed description of the preferred embodiments and accompanying drawings.

BRIEF DESCRIPTION OF THE DRAWINGS

FIGS. 1A through 1H illustrate the general structure and operation of a first embodiment of the present invention.

FIGS. 6A and 6B are detailed cross sectional views illustrating the general structure and operation of an alternate embodiment of a needle delivery and capture system.

FIGS. 6C and 6D are detailed cross sectional views illustrating the general structure and operation of another alternate embodiment of a needle delivery and capture system.

FIG. 7 is a projected detail view taken along the lines of view 7—7 of FIG. 6A illustrating the needle catch.

FIG. 8 is a cross sectional view taken along the lines of 8—8 on FIG. 7.

FIG. 9 is a detailed perspective view illustrating the general structure of an alternate embodiment of the needle carrier and guide track.

FIG. 9A is a detailed perspective view illustrating the general structure of an alternate embodiment of the needle carrier.

FIGS. 11A and 11B are cross sectional views of two alternate designs of the needle carrier taken upon the lines of 11—11 on FIG. 9.

FIG. 12 is a cross sectional view of the needle carrier and guide track taken upon the lines of 12—12 on FIG. 10.

FIG. 13 is a cross sectional view of the needle carrier and guide track taken upon the lines of 13—13 on FIG. 10.

FIGS. 17A–17D illustrate the operation of the embodiment described in FIGS. 14–16.

FIGS. 18A–18B are detailed perspective views of the distal tip of the device illustrating the general structure and operation of the axial articulation of the needle driver head.

DETAILED DESCRIPTION OF THE PREFERRED EMBODIMENTS

Figure 2:
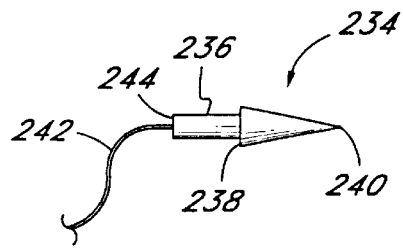
FIG. 2 is a detail plan view of a needle.

Although the principles of the present invention are applicable to any device suitable for use in surgical procedures, whether performed on humans or animals, particular utility is effected in human abdominal surgery performed using endoscopic techniques for closure of the wounds created during the introduction of trocars into the abdominal cavity, and particularly the puncture wounds created thereof, as well as closure or approximation of the wounds created either during the resection of benign or malignant lesions, or during the performance of other therapeutic procedures on an organ or organs within a body cavity.

FIGS. 1A through 1H illustrate the general structure and operation of a first embodiment of the present invention. FIGS. 1A and 1B show a device 2, according to the present invention, which incorporates a length of standard suture material 4 with a needle 6 on each end. The needles 6 are held by a needle carrier 8 (FIG. 1D) and loaded into two guiding tracks 10. The guiding tracks 10, containing the needle carriers 8 and needles 6, are deployable outside a housing 12 of the device 2 to allow the suture material 4 to be placed outside the limits of a puncture wound 14 (FIGS. 1B and 1C). After deployment of the guiding tracks 10 (with the needle carriers 8 and needles 6 contained within) the needle carriers 8 and needles 6 are driven out of the guiding tracks 10 and into tissue surrounding the puncture wound 14 (FIGS. 1C and 1D). The needles 6 are driven into a catch mechanism 16 (FIG. 1D). The needle carriers 8 are retracted back into the guiding tracks 10 (FIG. 1E). The guiding tracks 10 (now containing only the needle carriers 8 without the needles 6) and the catch mechanism 16 with the captured needles 6, are retracted as shown in FIGS. 1F, 1G and 1H. With a loop of suture 4 having thus been placed in the tissue surrounding the puncture wound 14, the suture device 2 is removed from the wound 14, thereby pulling the ends of the suture 4 with it (FIG. 1H). Closure of the puncture wound 14 is accomplished by cutting the suture 4 to remove the needles 6, tying a knot in the suture 4, and pushing it into the wound 14. Superficial closure is then performed by normal means according to the surgeon's preference.

Figure 3:
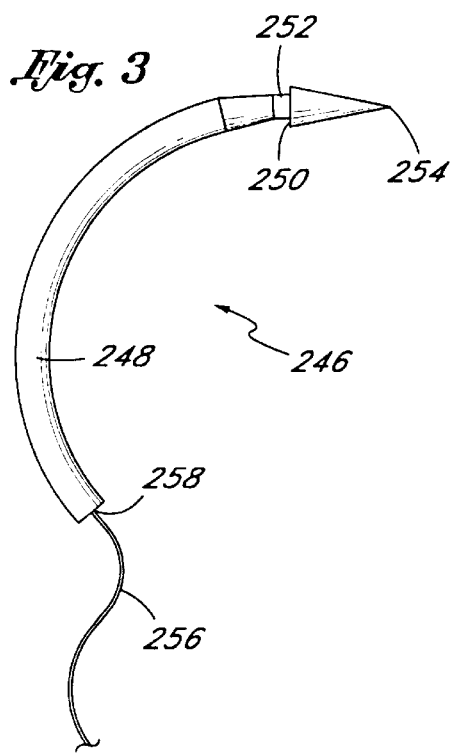
FIG. 3 is a detail plan view of an alternate needle.

FIGS. 2 and 3 show detail plan views of alternate needle embodiments. Referring to FIG. 2, a needle 234 comprises a body 236, and a shoulder 238 tapering to a point 240. A length of suture material 242 is inserted into a hole 244 and attached to the needle 234 thereby. Referring now to FIG. 3, a needle 246 comprises a body 248 and a shoulder 250 formed by a groove 252 which tapers to a point 254. A length of suture material 256 is inserted into a hole 258 and attached to the needle 246 thereby.

Figure 4:
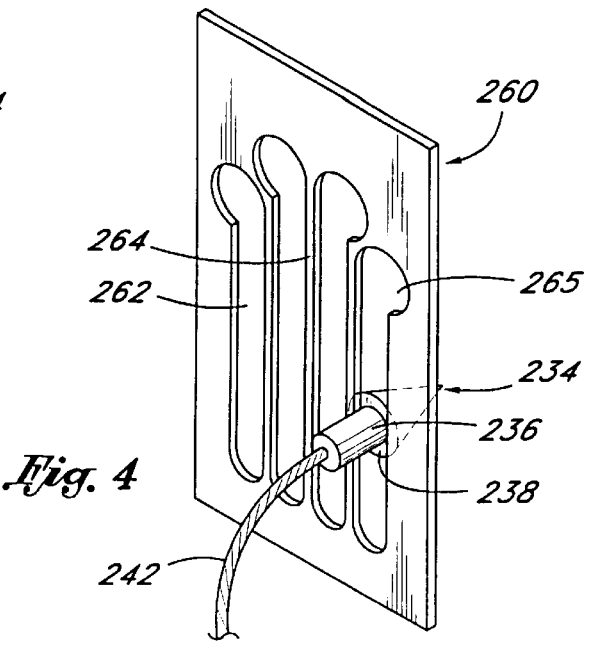
FIG. 4 is a detail perspective view of a catch mechanism with a needle.
Figure 5:
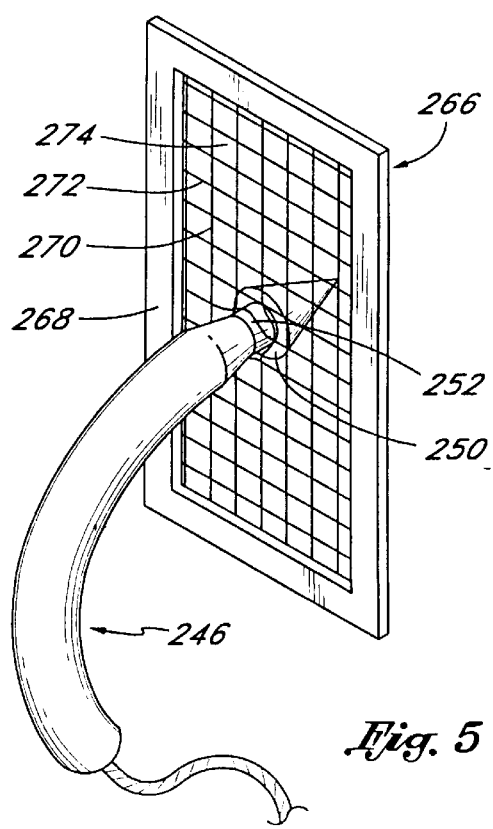
FIG. 5 is a detail perspective view of an alternate catch mechanism with a needle.

FIGS. 4 and 5 show detail perspective views of alternate catch embodiments and illustrate their operation. A catch 260 is preferably constructed of thin stainless steel of high temper, such as ANSI 301 full hard. Although the catch 260 may be fabricated by means of stamping or laser machining, the preferred method is by chemical etching. Referring to FIG. 4, the catch 260 includes openings 262 defined by ribs 264. As the needle 234 enters the opening 262, the ribs 264 deflect slightly to allow the shoulder 238 to pass through. After the shoulder 238 has passed the ribs 264, the ribs spring back to their original position defining the openings 262. The openings 262 are chosen to be smaller in dimension than the shoulder 238. This causes the catch 260 to retain the needle 234 by the interference between the shoulder 238 and the ribs 264 around the body 236. When it is necessary to remove the needle 234 from the catch 260, it may be moved toward an opening 265 which is sized to allow the needle shoulder 238 to pass through without resistance.

Referring now to FIG. 5, a catch 266 includes a frame 268 to which is attached a woven mesh 270. Threads 272 creating the woven mesh 270 may be made out of nylon, polyester or the like woven in a common over/under pattern. The weaving of the threads 272 creates holes 274 in the mesh through which a needle 246 may be passed. The needle 246 is constructed such that the shoulder 250 defined by the groove 252 is larger than the holes 274, or conversely, the holes 274 are chosen to be smaller than the shoulder 250. The point 254 of the needle 246 pushes the threads 272 aside creating room for the shoulder 250 to pass through the holes 274. As the threads 272 return to their original positions, the catch 266 holds onto the needle 246 by means of the mismatch in the size of the holes 274 and the shoulder 250.

It may be seen and should be understood that catches 260 and 266 are capable of catching either needle 234 or 246. The examples of needle 234 coupled with catch 260 and needle 246 coupled with catch 246 are given purely to illustrate the concepts of each embodiment and do not exclude their coupling with alternate designs.

Yet another embodiment of the invention is an alternate needle driver and catch system as shown in FIG. 6A and FIG. 6B, which are detailed cross sectional views of the distal end of the suture application system. Referring to FIG. 6A an elongate cannular body 718 is comprised of the housing halves 720 a,b. It is to be understood that for clarity only one of the housing halves 720 of the cannular body 718 is shown in FIG. 6A and FIG. 6B. The housing halves 720 are configured to create a guided pathway 722 which is comprised of a needle carrier guide track 724 and a flexible carrier driver guide track 726. A needle carrier 728 and flexible carrier driver 730 are joined at an end 732 of the needle carrier 728. The attachment between the needle carrier 728 and the flexible carrier driver 730 at the end 732 can be accomplished by crimping, welding, adhesive bonding or various other techniques. A bullet needle 734 includes a shoulder 736, a point 738 and a shaft 740. A length of suture material 742 is attached to the shaft 740 by placing it in a hole 744 and holding it there by suitable means, such as crimping or adhesive bonding or the like. Further incorporated in the housing halves 720 are catch pockets 746 a,b which position and retain a needle catch 748. Referring to FIG. 7, which is a detail plan view taken along the lines of 7—7 of FIG. 6A, it may be seen that the needle catch 748 includes openings 750 defined by ribs 752. The configuration and function of the needle catch 748 is similar to that described earlier in FIG. 4. The bullet needle 734 is inserted into an end 754 of the needle carrier 728. The shoulder 736 of the bullet needle 734 rests on the end 754 of the needle carrier 728, the end 754 dimensioned to hold and retain the bullet needle 734 in a manner previously described. When the catch 748 is fabricated by means of chemical etching, the most preferred method is to etch from a single side, known in the art as single sided etching. When the catch 748 is etched from a single side, the ribs 752 have a tapered cross section 753 as shown in FIG. 8, which is a detail cross sectional view taken along the lines of 8—8 of FIG. 7. The tapered cross section 753 helps to guide the needle 734 into the catch openings 750, minimizing the chance of the needle 734 hitting the top of the ribs 752.

Referring now to FIGS. 6A and 6B, the operation of this embodiment will be described. It is to be understood that the function of this embodiment is similar to that previously described in FIGS. 1A through 1H, that is, to approximate and close the puncture wounds created when surgical trocars are introduced into a body cavity. For clarity, the imposition of tissue planes along the path of needle travel to be described in FIGS. 6A and 6B has not been shown, although it is implied. FIG. 6A shows the bullet needle 734 loaded into the needle carrier 728 which is depicted in the retracted position. In this position, the cannular body 718 may be passed through a surgical trocar and into a body cavity for operation of the device. As shown in FIG. 6B, as the flexible carrier driver 730 is advanced into the needle carrier guide track 724, the needle carrier 728, holding the bullet needle 734 and trailing the suture 742 is driven on a semi-circular path terminating in the needle catch 748. The bullet needle 734 is captured by the catch 748 in a manner previously described in FIG. 4. The flexible carrier driver 730 may be retracted back into the flexible carrier driver guide track 726, causing the needle carrier 728 to rotate back into the needle carrier guide track 724 in the body half 720. The instrument may be removed from the surgical trocar, and the process repeated on the other side of the wound. After knots have been tied, an approximation of the puncture wound is accomplished. It may be seen that a knot pusher may be incorporated into the distal end of this embodiment of the suture applicator to effect the tying of knots for approximation of the puncture wounds. As such, the knots would be pushed directly into the wound, and not necessarily through the surgical trocar.

Yet another embodiment of the invention is an alternate needle driver and catch system as shown in FIG. 6C and FIG. 6D, which are detailed cross sectional views of the distal end of a suture application system and are similar in construction to those already described in FIGS. 6A and 6B. Referring to FIG. 6C, an elongate cannular body 770 is comprised of housing halves 772 a,b. It is to be understood that for clarity only one of the housing halves 772 of the cannular body 770 is shown in FIG. 6C and FIG. 6D. The housing halves 772 are configured to create a guided pathway 774 which is comprised of a needle carrier guide track 776 and a flexible carrier driver guide track 778. A needle carrier 780 and flexible carrier driver 782 are joined at saddle 784 of the needle carrier 780. The saddle 784 comprises a channel, groove or opening formed in the proximate end of the needle carrier 780 into which the flexible carrier driver 782 may enter circumferentially as opposed to axially. The attachment between the needle carrier 780 and the flexible carrier driver 782 at the saddle 784 can be accomplished by crimping, welding, adhesive bonding or various other techniques. A bullet needle 786 includes a shoulder 788, a point 790 and a shaft 792. A length of suture material 794 is attached to the shaft 792 by placing it in a hole 796 and holding it there by suitable means, such as crimping or adhesive bonding or the like. Further incorporated in the housing halves 772 are catch pockets 798 a,b which position and retain a needle catch 800. The configuration and function of the needle catch 800 is similar to that described earlier in FIG. 4. The bullet needle 786 is inserted into an end 802 of the needle carrier 780. The shoulder 788 of the bullet needle 786 rests on the end 802 of the needle carrier 780, the end 802 dimensioned to hold and retain the bullet needle 786 in a manner previously described.

Although the operation of this embodiment is virtually identical to that described in FIGS. 6A and 6B, there are improvements included in this embodiment to the overall operation of the suture system. Referring back to FIGS. 6A and 6B, as it may be appreciated, as the needle carrier 728 approaches the end of its stroke, as illustrated in FIG. 6B, the circumferential length of the needle carrier 728 left inside the needle carrier guide track 724 is quite minimal. This can allow the needle carrier 728 holding the needle 734 to drift off of the pre described arcuate path which terminates in the needle catch 748. This drift may allow the needle 734 to miss the catch 748, causing an incomplete suturing cycle. It is desirable, then, to increase the circumferential length of the needle carrier left inside the guide track in order to improve the guidance of the needle carrier.

Accordingly, the embodiment illustrated in FIGS. 6C and 6D shows the needle carrier 780 with the saddle 784. The saddle 784 allows the flexible carrier driver 782 to exit from the needle carrier 780 at a point along the circumference, rather than at a distal end 804. This may be seen to increase the overall arc length of the needle carrier 780 when compared with the needle carrier 728 shown in FIG. 6A. As a result, when the flexible carrier driver 782 is slidably moved in the guided pathway 774, and the needle carrier 780 is caused to rotate within the needle carrier guide track 776, it may be seen by referring to FIG. 6D that when the bullet needle 786 enters the needle catch 800, a significantly larger portion of the needle carrier 780 is still captured within the needle carrier guide track 776. This may be seen to provide additional guidance to the needle carrier 780 as it penetrates tissue. It may also be seen that the geometry described above allows for a longer stroke length, and therefor greater tissue bite.

As it may be appreciated by those skilled in the art, during the performance of a surgical procedure where suturing of body tissues is required, it is often necessary to lift or twist the tissue planes with the needle in order to approximate them in their final positions. This lifting and/or twisting can place significant stresses on the needle, and indeed, breakage of needles in the operative field is a fairly common event. In the embodiments just described, the "needle" is the combination of, for example in FIG. 6C, the needle carrier 780 and the bullet needle 786. In this example, the majority of the induced stresses are absorbed by the needle carrier 780. In addition to provisions for leaving a more substantial portion of the needle carrier in the guide track for additional guidance, FIGS. 9 through 13 now describe an alternate embodiment of the needle carrier and guide track which further improves the guidance and resistance to deflection due to the stresses just described.

Referring now to FIG. 9, there may be seen the distal end of an elongate cannular body 858 which is comprised of housing halves 860 a,b. It is to be understood that for clarity only one of the housing halves 860 of the cannular body 858 is shown in FIG. 9. The housing halves 860 are configured to create a guided pathway 862 which is comprised of a needle carrier guide track 864 and a flexible carrier driver guide track 866. A needle carrier 868 includes a saddle 872, to which is attached a carrier bearing 874. The saddle 872 comprises a channel, groove or opening formed in the proximate end of the needle carrier 868 into which the flexible carrier driver 870 may enter circumferentially as opposed to axially. That is, at the intersection of the flexible carrier driver guide track 866 and the needle carrier guide track 864, lines which are tangent to the flexible carrier driver guide track 866 and the needle carrier guide track 864 are substantially parallel.

The construction of the needle carrier may be best understood by referring to FIG. 11A, where a cross sectional view shows the needle carrier 868 and the carrier bearing 874. The carrier bearing 874 further includes bearing wings 876 a,b. The carrier bearing 874 may be joined by welding, adhesive bonding or the like to the needle carrier 868.

The needle carrier 868 may also be formed by another method. FIG. 11B shows a cross sectional view of a needle carrier 878 which has been formed out of, for example, a 17-4 stainless steel alloy by a process called metal injection molding. This process allows the needle carrier 878 to be formed in a monolithic fashion such that bearing wings 880 a,b and saddle 882 may be formed in one piece, along with other features of the needle carrier previously described. Other processes, such as die casting, investment casting, or powdered metal could also be used to create a monolithic needle carrier 878.

Another embodiment of the needle carrier is shown in FIG. 9A, where there is shown a needle carrier 885 which includes a socket 886 at the distal end adapted to hold a shouldered needle and a groove 887 at the proximal end adapted to contain a flexible needle driver 888 as previously described. Pins 889 a,b,c,d are attached to the sides of the needle carrier 885. The pins 889 are dimensioned to be slidably disposed within, referring to FIG. 9, the groove 884 in the needle carrier guide track 864, and to provide guidance and stability to the needle carrier 885 in a fashion similar to that to be described with reference to FIG. 9 below.

Referring again to FIG. 9, the needle carrier 868 and flexible carrier driver 870 are joined as previously described at saddle 872 of the needle carrier 868, which incorporates bearing wings 876 a,b. The distal end 882 of the needle carrier 868 is adapted to accept a shouldered bullet needle of the type previously described in other embodiments. In this embodiment, the needle carrier guide track 864 further incorporates a groove 884 adapted to receive the bearing wings 876 a,b. By referring to FIG. 12, a detailed cross sectional view of the groove 884 and the bearing wings 876, taken along the lines of the section arrows 12—12 shown in FIG. 10, may clearly be seen. FIG. 13 is a detailed cross sectional view of the needle carrier guide track 864 taken along the lines of the section arrows 13—13 shown in FIG. 10, and illustrates an area of the needle carrier 868 and of the needle carrier guide track 864 where there are no bearing wings 876 a,b. It should be understood that the cross section shown in FIG. 13 of the needle carrier 868 could be of solid material instead of tubular material if the cross section were illustrating a monolithic part such as the needle carrier 878. It may also be understood from the foregoing illustrations, that the width and depth of the bearing wings 876 *a,b* shown in FIG. 11A and the bearing wings 880 *a,b* shown in FIG. 11B are not to be taken as literal illustrations of the physical dimensions of those features, as the width and depth may be varied in order to achieve more or less guidance and bearing surface area as the designer deems appropriate.

The operation of the embodiment described in FIGS. 9 through 13 is identical to that previously described in FIGS. 6C and 6D, with the exception that the bearing wings 876 *a,b* are adapted to rotationally slide in the grooves 884 *a,b* of the housing halves 860 *a,b*. This provides axial and torsional guidance and resistance to deflection of the needle carrier 868 from the anticipated path. Performance improvements over the embodiment described in FIGS. 6C and 6D relate primarily to an increased ability to be able to torque and/or lift the device while the needle carrier is exposed to the tissues to be sutured.

The preferred material for the flexible carrier driver 870 is an alloy of nickel and titanium known in the art as nitinol. This material has both austenitic and martensitic forms, and can be alloyed to exhibit properties of both forms as the material moves through a transition temperature that can be varied. The martensitic form of the alloy, when processed into, for example, wire, has a lead-solder like consistency, and easily deflects plastically to a certain point, beyond which a considerable amount of force is necessary to cause further deflection. This elastic behavior in this regime is what allows the material to be both flexible and exhibit high column strength when properly constrained. As long as the wire is not required to bend around a radius which deflects the material past the plastic limit, the wire does not offer significant spring force. However, if it is required that the wire be bent around a tight radius, and the wire enters the elastic part of the stress/strain curve, substantial spring force may be exhibited. Thus in this application, the material is used in the regime that exhibits high column strength for the purposes of driving the needle. This is accomplished by constraining the wire in a track that allows it to be moved axially, but constrains its deflection off axis.

TRANSVAGINAL SUTURING EMBODIMENT

Yet another embodiment of the invention may be seen by now considering FIGS. 14–18. There may be seen an alternate embodiment of the present invention which is particularly well suited for but not limited to the fixation of sutures to the Cooper's ligament during the performance of a Burch bladder neck suspension via a transvaginal approach. As will become apparent, this embodiment includes features for limiting the depth of the needle penetration for placing sutures in, for example, ligaments lying directly on bone, and for accommodating the anatomy of, for example, the female pelvis.

Figure 14:
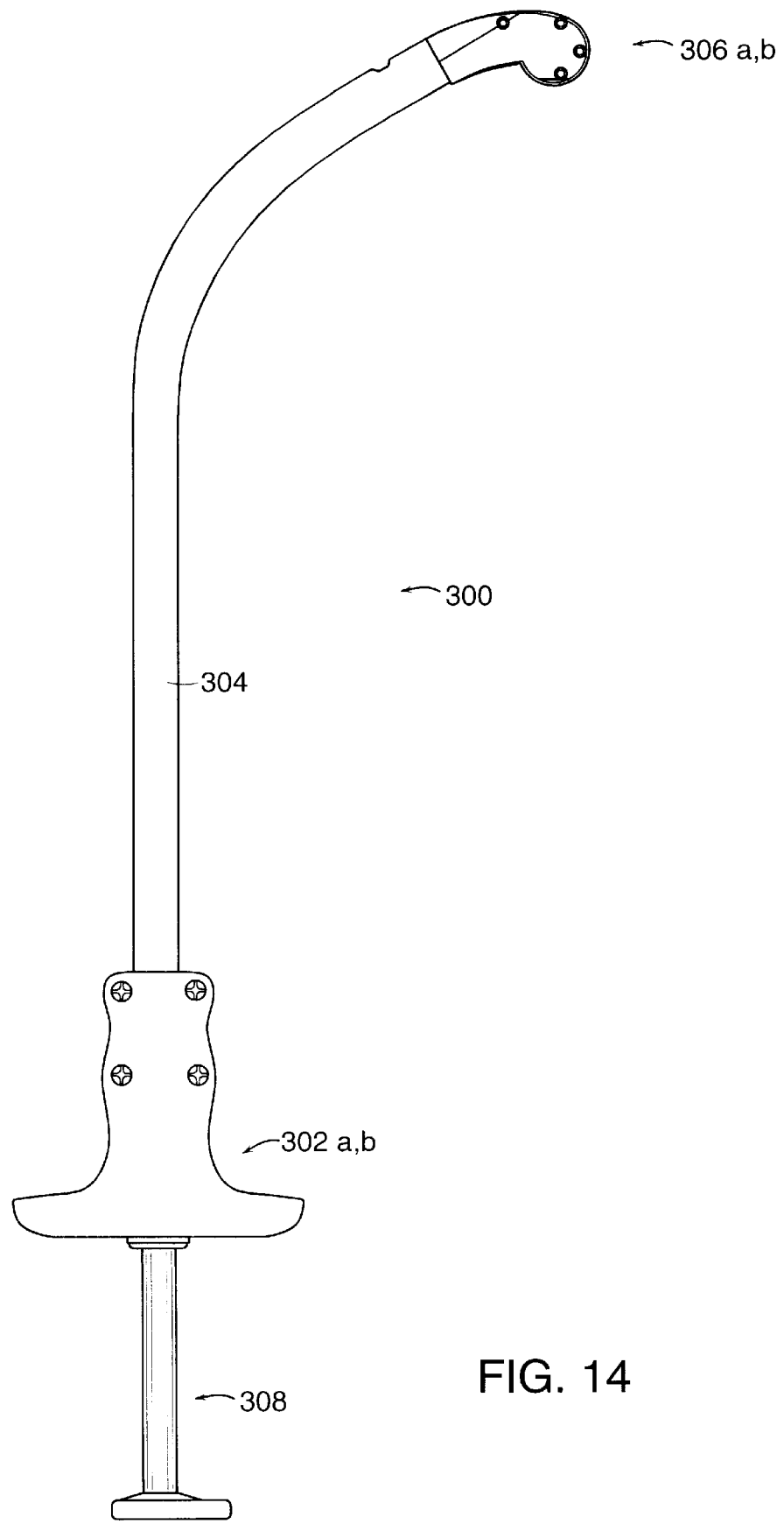
FIG. 14 illustrates the general structure of another embodiment of the present invention.
Figure 15:
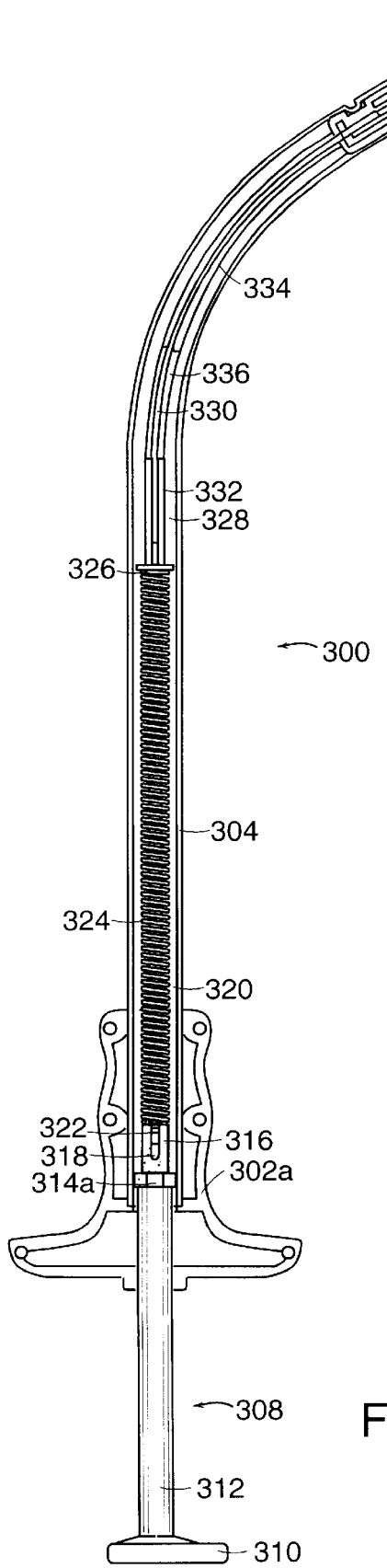
FIG. 15 is a cross sectional view illustrating the general internal structure of the embodiment described in FIG. 14.

Referring now to FIG. 14, there may be seen a suturing instrument 300 which includes handles 302 *a,b*, an elongate body 304, distal tips 306 *a,b*, and an actuator button 308. Again, for purposes of clarity, FIG. 15 is a detailed cross section of FIG. 14 illustrating the internal components that will now be detailed. Referring now to FIG. 15, there may be seen a cross sectional view of the suturing instrument 300 which includes the handle 302*a*, the elongate body 304, the distal tip 306*a*, and the actuator button 308. The actuator button 308 includes a button head 310, a button shaft 312, button bearing surfaces 314 *a,b,c,d*, button end 316, and hole 318. The button bearing surfaces 314 ride along a cylindrical surface 320 that is formed by the inside diameter of the elongate body 304. A wireform 322 is inserted into the hole 318, coupling it to the actuator button 308. A spring 326 encircles the wireform 322, abuts the button end 316, and is compressed between the button end 316 and a spring washer 326, which spring washer 326 is seated upon a center tube 328. The center tube 328 is housed by the cylindrical surface 320, and is constrained at the distal end by the distal tips 306. A pusher wire 330 is attached to the wireform 322 by means of a weld, a coupling, adhesive or other means, and is slidably disposed within a proximal guidance sleeve 332 and a distal guidance sleeve 334, said sleeves 332 and 334 being disposed within a cylindrical surface 336 formed by the inside diameter of the center tube 328.

The pusher wire 330 is preferably constructed of nitinol wire, so chosen as previously discussed for its combination of properties that allow for bendability and high column strength when constrained. The constraints in this construction are provided by the proximal guidance sleeve 332 and the distal guidance sleeve 334.

Figure 16:
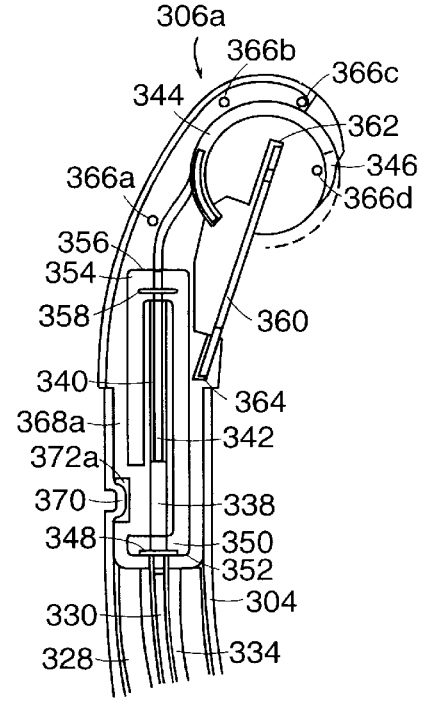
FIG. 16 is a detailed cross sectional view of the head of the embodiment described in FIGS. 14 and 15.

An overview of the general structure of this embodiment may be understood by considering now FIG. 16, which is a detailed cross sectional view of the distal end of the suturing device 300. It is to be understood for the purposes of clarity, that only one of the distal tips 306 is shown, and that cross sectional representations of the center tube 328, the distal guide tube 334, and the elongate outer tube 304 are shown. From FIG. 16, it may be seen that the nitinol pusher wire 330 is attached by welding or other means to a coupling 338, which is slidably disposed within a track 340, the coupling 338 also being attached to a carrier wire 342, which by virtue of its attachment to the coupling 338 is also slidably disposed within the track 340. The carrier wire 342 is attached to a carrier 344 by welding or other means, said carrier being rotatably and slidably disposed within a guide groove 346 molded into the distal tip 306. The relationship between the carrier wire 342, the carrier 344 and the guide groove 346 is similar to that previously described in FIGS. 9–13. The coupling 338 abuts a backstop washer 348 that is slidably disposed about the nitinol pusher wire 330, and contained within a pocket 350 which includes a back wall 352, against which the backstop washer 348 rests.

The track 340 terminates distally in a pocket 354 that includes a wall 356. A downstop washer 358 is slidably disposed about the carrier wire 342, and constrained within the pocket 354. Positioned at the terminus of the path of the carrier 344 is a needle catch 360 that is held distally in a pocket 362 and proximally in a pocket 364. As will be seen in the description of the application of this embodiment, this needle catch 360 is similar in construction and function to the catch described in FIGS. 4, 7, and 8. As previously described in other embodiments, the distal tips 306 *a,b* are held together by rivets placed in rivet holes 366 *a,b,c,d* and by tip shafts 368 *a,b* being inserted into the cylindrical surface 320 which is the inside diameter of the elongate body 304. A depression 370 in the elongate body 304 may be formed by mechanical means such as striking with a pin or forming with a die. The depression 370 is engaged in a rotation pocket 372 *a,b* that is formed as a feature of the distal tips 306 *a,b*, and will be further described in FIGS. 18A–18B.

Referring now to FIGS. 17A–17D, the operation of this embodiment may be appreciated. Although this description attests to a specific application for the performance of a Modified Burch bladder neck suspension via a transvaginal approach, it is to be understood that the principles and construction herein described may be applied to other areas of the human body, and for other procedures requiring suturing body structures such as ligaments that are in direct communication with bone. That understood and considering FIGS. 17A–17D, there may be seen a sequence of operation of the current embodiment. Referring to FIG. 17A there may be seen a detailed cross sectional view of the distal tip of the suturing device 300. The suturing device 300 is shown with a suture 374 attached to a suture needle 376 in a manner similar to that described in FIG. 2 and is shown loaded into the carrier 344 in preparation for actuation. The suturing device 300 has been placed against a ligament 378 that lies directly on a bone 380. Referring back to FIG. 15 together with FIG. 17A, it may be seen that the pusher wire 330 is held in tension by the spring 324, as the coupling 338 shown in FIG. 17A abuts the backstop washer 348 that is held against the back wall 352, positioning the needle carrier 344 in its most proximal or rearward location.

As those skilled in the art will appreciate, it is quite difficult to drive a suture needle through a ligament that lies directly on bone, as the bone's density does not allow a typical suture needle to penetrate it. Thus a skimming path must be taken to avoid hitting bone, but ensuring good penetration of the ligament and a subsequent "good bite" of tissue. In the case of the Cooper's ligament that is the focus of the anterior fixation point for the Modified Burch bladder neck suspension procedure, the difficulty in placing those sutures is directly attributable to the ligament lying on the bone, and the problems with exposure of the ligament to the surgeon.

Again referring to FIG. 15 and now FIG. 17B, the actuator button 308 is depressed by pushing on the button head 310, which via the attachment to the wireform 322 which is attached to the pusher wire 330, moves the coupling 338 shown in FIG. 17B along the track 340, concomitantly moving the carrier wire 342 which slidably and rotatably moves the carrier 344 in the guide track 346 and drives the suture needle 376 trailing the suture 374 into the ligament 378. It may be seen in this FIG. 17B that the suture needle 376 is skimming or sliding along the surface of the bone 380, maximizing the depth of penetration but not digging in or penetrating the bone surface. This superficial, i.e., shallow penetration, needle driving geometry results in a unique needle delivery system.

Referring now to FIG. 17C, it may be seen that as the pusher wire 330 responds to greater urging of the button 308, the coupling 338 reaches a point in its travel along the track 340 where it pushes the downstop washer 358 such that it abuts the wall 356 of the pocket 354. This action limits the outward travel of the carrier 344 to prevent overdriving and eliminate the possibility of expelling the carrier 344 from the distal tips 306. The suture needle 376 trailing the suture 374 is driven through the ligament 378 and into the needle catch 360, where it is captured in a manner previously described. As the button 308 is released, the spring 324 urges the button 308 proximally, moving the pusher wire 330, the coupling 338, the carrier wire 342 and the carrier 344 proximally along with it to the position shown in FIG. 17D, where the backstop washer 348 arrests the proximal movement in a manner previously described, leaving the suture needle 376 in the needle catch 360 and the suture 374 driven through the ligament 378.

Figure 10:
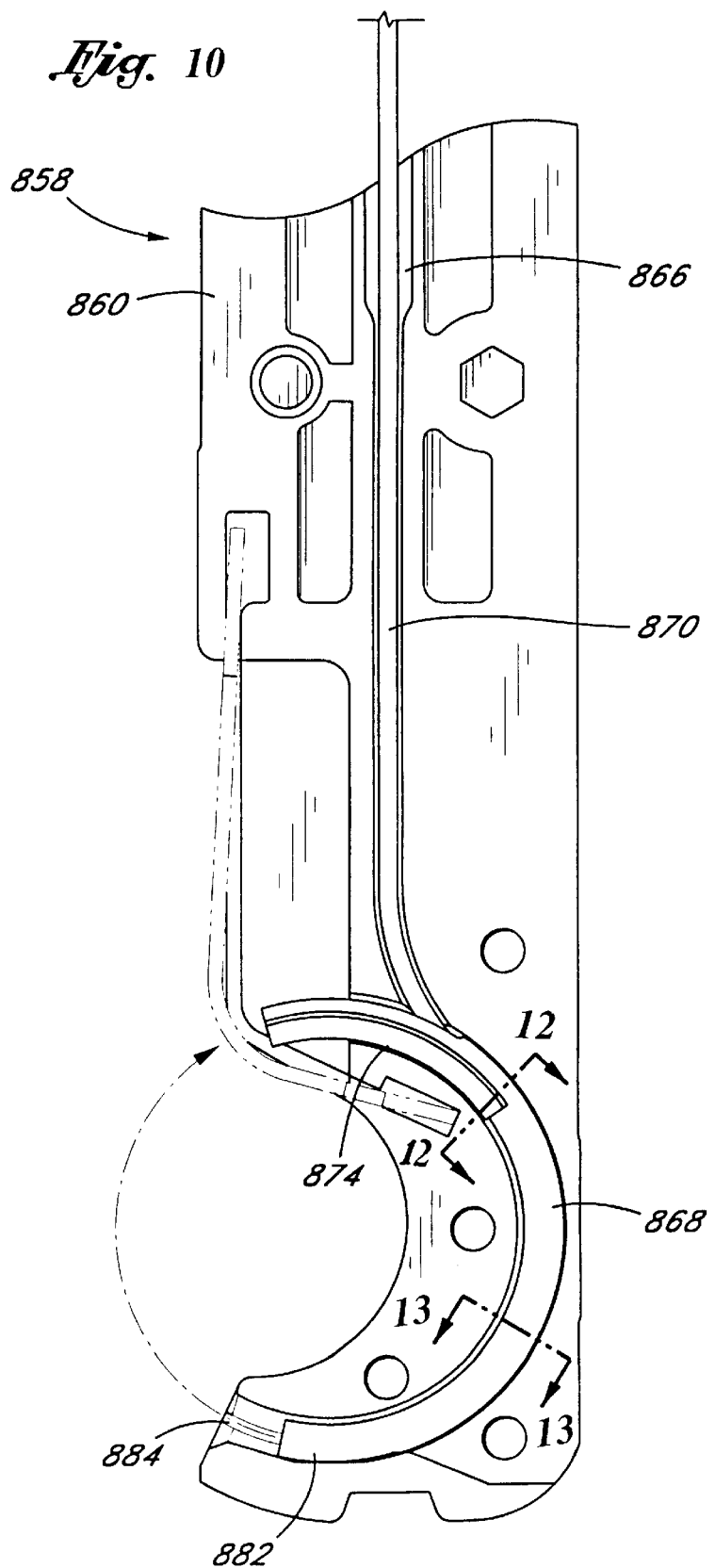
FIG. 10 is a detailed cross sectional view illustrating the relationship between the needle carrier and guide track.

A differentiation of this embodiment may be seen by referring to FIGS. 10 and 16. In the embodiment shown in FIG. 10, the path of the needle carrier 868, illustrated by a phantom line in FIG. 10, exits the housing 860 in a direction which is substantially perpendicular to the surface of the housing 860 and presents an opportunity for the needle carrier 868 to be driven directly into the tissue surface placed against the exit. Thus, if there were bone immediately underlying that tissue, this would allow a needle loaded into the needle carrier 868 to be driven directly into bone. In the embodiment shown in FIG. 16, a different type of carrier path is illustrated by a phantom line. In this embodiment, the carrier path exits the distal tip 306 in a direction which approaches being substantially tangential to the surface of the distal tip 306. This substantially tangential exit path allows this instrument to achieve the skimming tissue bite referred to earlier. As shown in FIGS. 17A–17D, when the surface surrounding the exit port of this device is placed next to a tissue surface, a needle loaded into the carrier 344 takes a skimming tissue bite, thereby minimizing any possible penetration of bone underlying the tissue.

Another aspect of this embodiment which is advantageous to the function of the device is the ability to rotate the distal tips 306 of the instrument relative to the elongate body 304, allowing the instrument to conform to the contours of, for example, the pelvic brim. This is accomplished by incorporating a construction such as that illustrated in FIGS. 18A–18B. For clarity, the elongate body 304 has been shown in section view in order that the depression 370 may be seen to engage the rotation pockets 372 a,b. This engagement couples the distal tips 306 a,b to the elongate body 304, as previously described, and also allows the assembly of the distal tips 306 a,b to be rotated axially along the cylindrical surface 320.

As previously described, in any surgical procedure, or in fact in any application that utilizes a needle and thread, the needle is simply a vehicle that carries the suture or thread through the tissue or media to be sewn. As such, there may be contemplated alternate methods for transporting the suture through the tissue that may also incorporate the specific features of, for instance, skimming bite or flexible drive. These alternate methods are to be included within the scope of the present invention. For example, one such method not previously discussed would involve a needle with an eye near the distal end of the needle, a configuration not unlike that seen in a traditional sewing machine. In such a construction, the suture could be threaded into the eye of the needle, and the needle driven through the tissue with a capture mechanism for the suture at the end of the path. The needle could then be withdrawn, leaving the suture in situ. Such a configuration would be well within the scope of the previously described invention if it incorporated features herein described such as, for instance, skimming bite or flexible drive.

It will be understood that the apparatus and method of the present invention for an endoscopic suture system may be employed in numerous specific embodiments in addition to those described herein. Thus, these numerous other embodiments of the invention, which will be obvious to one skilled in the art, including but not limited to changes in the dimensions of the device, the type of materials employed, the location and type of needles, driving mechanisms, catching mechanisms, needle loading mechanisms, etc., are to be included within the scope of the present invention. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A suturing instrument comprising:
an elongate body member having a longitudinal axis;
a suture deployment system located within a distal end portion of said elongate body member wherein said distal end portion includes a suture exit port, said suture deployment system comprising:
a curved suture carrier channel; and
a curved suture carrier movably positioned in said curved suture carrier channel;
and
a deployment controller having a proximal end, a distal end, a retracted position and a deployed position, said deployment controller extending substantially along the longitudinal axis of said elongate body member to the distal end of said elongate body member where it is coupled to said curved suture carrier and moves said curved suture carrier through said curved suture carrier channel as it moves between said retracted position and said deployed position, said curved suture carrier channel configured within said distal end portion of said elongate body member such that said curved suture carrier exits said suture exit port and is guided along a path which includes a proximal curved path segment such that a surface of said curved suture carrier is substantially adjacent with an outer surface of said distal end portion of said elongate body member along said proximal curved path segment.

2. A suturing instrument as defined in claim 1 further comprising a suture catch positioned proximate to said distal end portion of said elongate body member such that a distal path segment of said curved suture carrier path is intercepted by said suture catch as said deployment controller approaches said deployed position.

3. A suturing instrument as defined in claim 1 further comprising a surgical needle positioned in a distal end of said curved suture carrier.

4. A suturing instrument as defined in claim 3 wherein said surgical needle further comprises a bullet needle.

5. A suturing instrument as defined in claim 1 wherein:
said curved suture carrier channel and said curved suture carrier are located in a distal tip assembly of said elongate body member; and
said distal tip assembly is joined with said elongate body member such that said distal tip assembly is free to rotate axially about said elongate body member longitudinal axis.

6. A suturing instrument as defined in claim 1 wherein said deployment controller is coupled to said curved suture carrier with a flexible driver member.

7. A suturing instrument as defined in claim 6 wherein said flexible driver member further comprises an alloy of nickel and titanium.

8. A suturing instrument comprising:
a body member;
a suture exit port formed in said body member;
a curved suture carrier channel formed in said body member; and
a curved suture carrier movably positioned in said curved suture carrier channel, wherein said curved suture carrier has a retracted position such that said curved suture carrier is positioned within an interior region of said body member and a deployed position such that a portion of said curved suture carrier is positioned exterior to said body member, said curved suture carrier configured within said curved suture carrier channel such that said curved suture carrier exits said interior region of said body member through said suture exit port and is guided along a path which includes a proximal curved path segment wherein a surface of said curved suture carrier is substantially adjacent with an outer surface of said body member along said proximal curved path segment.

9. A suturing instrument as defined in claim 8 further comprising a suture catch positioned on said body member such that a distal path segment of said curved suture carrier path is intercepted by said suture catch.

10. A suturing instrument as defined in claim 8 further comprising a surgical needle positioned in a distal end of said curved suture carrier.

11. A suturing instrument as defined in claim 10 wherein said surgical needle further comprises a bullet needle.

12. A suturing instrument comprising:
an elongate body member having a longitudinal axis;
a distal tip suture deployment assembly joined with a distal end of said elongate body member such that said distal tip assembly is free to rotate axially about said elongate body member longitudinal axis, said distal tip suture deployment assembly comprising:
a distal tip body member;
a suture exit port formed in said distal tip body member;
a curved suture carrier channel formed in said distal tip body member; and
a curved suture carrier movably positioned in said curved suture carrier channel;
and
a deployment controller having a proximal end, a distal end, a retracted position and a deployed position, said deployment controller extending substantially along the longitudinal axis of said elongate body member to the distal end of said elongate body member where it is coupled to said distal tip suture deployment assembly and moves said curved suture carrier through said curved suture carrier channel as it moves between said retracted position and said deployed position.

13. A suturing instrument as defined in claim 12 wherein said distal tip suture deployment assembly is configured to have a retracted position such that said curved suture carrier is positioned within an interior region of said distal tip body member and a deployed position where a portion of said curved suture carrier is positioned exterior to said distal tip body member, said curved suture carrier configured within said curved suture carrier channel such that said curved suture carrier exits said interior region of said distal tip body member through said suture exit port and is guided along a path which includes a proximal curved path segment wherein a surface of said curved suture carrier is substantially adjacent with an outer surface of said distal tip body member along said proximal curved path segment.

14. A suturing instrument as defined in claim 12 further comprising a suture catch positioned on said distal tip body member such that a distal path segment of said curved suture carrier path is intercepted by said suture catch as said deployment controller approaches said deployed position.

15. A suturing instrument as defined in claim 13 further comprising a suture catch positioned on said distal tip body member such that a distal path segment of said curved suture carrier path is intercepted by said suture catch as said deployment controller approaches said deployed position.

16. A suturing instrument as defined in claim 12 further comprising a surgical needle positioned in said distal end of said curved suture carrier.

17. A suturing instrument as defined in claim 16 wherein said surgical needle further comprises a bullet needle.

18. A method for placing a suture in thin tissue adjacent bone structure comprising:

placing a suturing instrument which encloses a curved suture carrier which is movably positioned within a curved suture carrier channel adjacent the tissue to be sutured; and deploying the curved suture carrier out of the suturing instrument through an exit port such that the curved suture carrier exits an interior region of said suturing instrument through said exit port along a path which approaches being substantially tangential to an outer surface of said suturing instrument surrounding said exit port.

19. A suturing instrument comprising:

a body member;

an exit port formed in said body member;

a curved suture carrier channel formed in said body member; and a curved suture carrier movably positioned in said curved suture carrier channel, wherein said curved suture carrier has a retracted position such that said curved suture carrier is positioned within an interior region of said body member and a deployed position such that a portion of said curved suture carrier is positioned exterior to said body member, said curved suture carrier configured within said curved suture carrier channel such that said curved suture carrier exits said interior region of said body member through said exit port along a path which approaches being substantially tangential to an outer surface of said body member surrounding said exit port.

20. A suturing instrument comprising:

an elongate body member having a longitudinal axis;

a suture deployment system located within a distal end portion of said elongate body member wherein said distal end portion includes a suture exit port, said suture deployment system comprising:

a curved suture carrier channel; and a curved suture carrier movably positioned in said curved suture carrier channel;

and a deployment controller having a proximal end, a distal end, a retracted position and a deployed position, said deployment controller extending substantially along the longitudinal axis of said elongate body member to the distal end of said elongate body member where it is coupled to said curved suture carrier and moves said curved suture carrier through said curved suture carrier channel as it moves between said retracted position and said deployed position, said curved suture carrier channel configured within said distal end portion of said elongate body member such that said curved suture carrier exits said suture exit port along a path which approaches being substantially tangential to an outer surface of said body member surrounding said suture exit port.

21. A suturing instrument as defined in claim 20 further comprising a suture catch positioned proximate to said distal end portion of said elongate body member such that a distal path segment of said curved suture carrier path is intercepted by said suture catch as said deployment controller approaches said deployed position.

22. A suturing instrument as defined in claim 20 further comprising a surgical needle positioned in a distal end of said curved suture carrier.

23. A suturing instrument as defined in claim 22 wherein said surgical needle further comprises a bullet needle.

24. A suturing instrument as defined in claim 20 wherein:

said curved suture carrier channel and said curved suture carrier are located in a distal tip assembly of said elongate body member; and said distal tip assembly is joined with said elongate body member such that said distal tip assembly is free to rotate axially about said elongate body member longitudinal axis.

25. A suturing instrument as defined in claim 20 wherein said deployment controller is coupled to said curved suture carrier with a flexible driver member.

26. A suturing instrument as defined in claim 25 wherein said flexible driver member further comprises an alloy of nickel and titanium.

* * * * *